(12) United States Patent
Hartell et al.

(10) Patent No.: US 6,951,846 B2
(45) Date of Patent: Oct. 4, 2005

(54) ARTEMISININS WITH IMPROVED STABILITY AND BIOAVAILABILITY FOR THERAPEUTIC DRUG DEVELOPMENT AND APPLICATION

(75) Inventors: Mark G. Hartell, Laurel, MD (US); Apurba K. Bhattacharjee, Silver Spring, MD (US); Rickey P. Hicks, Woodbridge, VA (US); John E. VanHamont, Fort Meade, MD (US); Wilbur K. Milhous, Germantown, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 34 days.

(21) Appl. No.: 10/376,387

(22) Filed: Feb. 27, 2003

(65) Prior Publication Data

US 2003/0203875 A1 Oct. 30, 2003

Related U.S. Application Data

(60) Provisional application No. 60/362,985, filed on Mar. 7, 2002.

(51) Int. Cl.[7] .................. C07D 519/00; A61K 31/357
(52) U.S. Cl. .................. 514/58; 514/60; 514/557; 514/772.2; 514/772.3; 514/773; 514/777; 514/779; 514/781; 514/54; 514/895; 514/23; 426/96; 424/440; 424/493; 424/500; 549/348; 536/103; 536/120; 536/122; 536/123.1
(58) Field of Search .................. 514/58, 54, 23, 514/60, 557, 772.2, 772.3, 773, 777, 779, 781, 895; 426/96; 424/440, 493, 500; 549/348; 536/103, 120, 122, 123.1

(56) References Cited

U.S. PATENT DOCUMENTS

| 6,586,464 B2 * | 7/2003 | Posner et al. ............. 514/450 |
| 2002/0147177 A1 | 10/2002 | Yuen et al. ............. 514/58 |

FOREIGN PATENT DOCUMENTS

| CH | 685391 A5 | 6/1995 |
| DE | WO/85 02767 | 12/1983 |
| WO | WO 01/62299 A2 | 2/2000 |

OTHER PUBLICATIONS

Usuda et al. "Interaction of Antimatarial agent artemisinin with cyclodextrins." Drug Development and Industrial Pharmacy, 26(6 613–19, 2000.*

Bayomi, M. "Characterization of Arteether Interactions with Beta–cyclodextrin and hydroxypropyl–beta–cyclodextrin", Saudi Pharmaceutical Journal, Saudi Pharm. Soc., vol. 10, No. 1/2, Jan. 2002, pp 36–43.

(Continued)

Primary Examiner—James O. Wilson
Assistant Examiner—Devesh Khare
(74) Attorney, Agent, or Firm—Elizabeth Arwine

(57) ABSTRACT

A stable form of artemisinin wherein an artelinic acid or artesunic acid is complexed with cyclodextrin analogs, preferably, β-cyclodextrin. The complexed cyclodextrin artemisinin formulation shields the peroxide portion of the artemisinin backbone from hydrolytic decomposition rendering it stable in solution. Artelinic acid and cyclodextrin are placed into contact with one another to yield a 2:1 molecular species. Artesunic acid and cyclodextrin yield a 1:1 molecular species. The complexed cyclodextrin artemisinin formulation is effective for the treatment of malaria and is stable in solution for long periods of time.

27 Claims, 30 Drawing Sheets

OTHER PUBLICATIONS

Usuda M., et al., "Interaction of antimalarial agent artemisinin with cyclodextrins", Drug Dev. and Industrial Pharmacy, New York, NY, US, vol. 26, No. 6, Jun. 2000, pp. 613–619.

Wong, J. et al., "Improved oral bioavailability of artemisinin through inclusion complexation with bets–and gamma–cyclodextrins", Internat. Jour. of Pharmaceutics, Amsterdam, NL, vol. 227, No. 1–2, 2001, pp. 177–185.

Szejtli, Cyclodextrin Technology, textbook, (1988) Kluwer Academic Publishers, p. 186–193, ISBN#90–227–2314–1.

Iiiapakurthy, et al. Abstract Interactionof artemisinin and its related compounds with hydroxypropyl–beta–cyclodextrin in solution state: Experimental and molecular–modeling studies. (2003).

* cited by examiner

ARTEMISININS WITH IMPROVED STABILITY AND BIOAVAILABILITY FOR THERAPEUTIC DRUG DEVELOPMENT AND APPLICATION

This application claims priority of provisional application No. 60/362,985 filed Mar. 7, 2002.

GOVERNMENT INTEREST

The invention described herein may be manufactured, used and licensed by or for the U.S. Government.

BACKGROUND OF THE INVENTION

1. Field of the Invention

A novel form of artemisinins that are complexed with cyclodextrin for solving stability problems associated with previous forms of artemisinins.

2. Brief Description of Related Art

Artelinic acid is an effective antimalarial agent when in contact with the malarial parasite. However, artelinic acid has poor stability in solution and, thus, has limited bioavailability in vivo. Artemisinins, as a class, include such analogs as artelinic acid and artesunic acid among many others. Currently, no analog of the artemisinin class of compounds exists which can remain stable in solution. Injectable formulations of artemisinin analogs, such as artelinic acid and artesunic acid, are not FDA approved due to their instability in solution. All artemisinins contain a peroxide bridge susceptible to hydrolytic cleavage. Artemisinins have been found to yield an inferior class of antimalarials due to these severe limitations in chemical stability. Artemisinins are limited to only being packaged as solids for oral dosing, as previous patents have claimed. U.S. Pat. Nos. 6,326,023; 6,307,068; 6,306,896; 5,834,491; 5,677,331; 5,637,594; 5,486,535; 5,278,173; 5,270,037; 5,219,865; 5,021,426; 5,011,951.

Application of an antimalarial formulation must be specific to administration in hot, humid tropical regions native to the malarial parasite. Thus, chemical stability under drastic environmental conditions is essential. Attempts to produce a more stable form of artelinic acid have been accompanied by critical limitations. A soluble sodium salt of artelinic acid has been successfully formulated, but eventually degrades over time. This is presumably due to a reformation of the insoluble acid. Numerous attempts at preventing this precipitate have been unsuccessful.

The osmolality of the salt solution is significantly less than the predicted value indicating possible inter-molecular complexation that may be responsible for eventual precipitation over time. An amine-based buffer of artelinic acid has been successfully formulated, but yields a higher pH solution (>8.0) that induces significant vein irritation upon injection. Additional localized redness and swelling surrounding the injection site is a notable contraindication to a preferred intravenous formulation. Additionally, amine-based buffers have been observed to take on a strong yellow hue over time. The mechanism of color formation has not been deduced, but implies a modification of the artelinate formulation, which is not conducive to pharmaceutical preparations where a defined constant state of purity is essential.

U.S. Pat. Nos. 6,326,023; 6,307,068; 6,306,896; 5,834, 491; 5,677,331; 5,637,594; 5,486,535; 5,278,173; 5,270, 037; 5,219,865; 5,021,426; 5,011,951 are only directed to be packaged as solids for oral dosing.

Therefore, there is a need to provide a form of artemisinins that solve the stability problems associated with previous formulations.

It is an object of the present invention to provide a form of artemisinins, such as but not limited to artelinic acid and artesunic acid that solves the stability problems associated with previous formulations.

It is another object of the present invention to provide a stable form of artemisinins that is injectable.

It is still another object of the present invention to provide a stable form of artemisinins that does not develop a yellow hue over time.

It is still another object of the invention to promote bioavailability and membrane permeability while decreasing the likelihood of localized inflammation at the route of entry, thus increasing its therapeutic activity.

These and other objects of the invention will become apparent upon a reading of the entire disclosure.

SUMMARY OF THE INVENTION

The present invention is directed to cyclodextrin complexed with artelinic acid or artesunic acid to form complexed cyclodextrin-artemisinin formulations in a 2:1 ratio of cyclodextrin per artelinic acid molecule or in a 1:1 ratio of cyclodextrin per artesunic acid molecule. The formulation is stable in solution, bioavailable, membrane permeable and does not cause inflammation upon injection.

DETAILED DESCRIPTION

Figure 1:
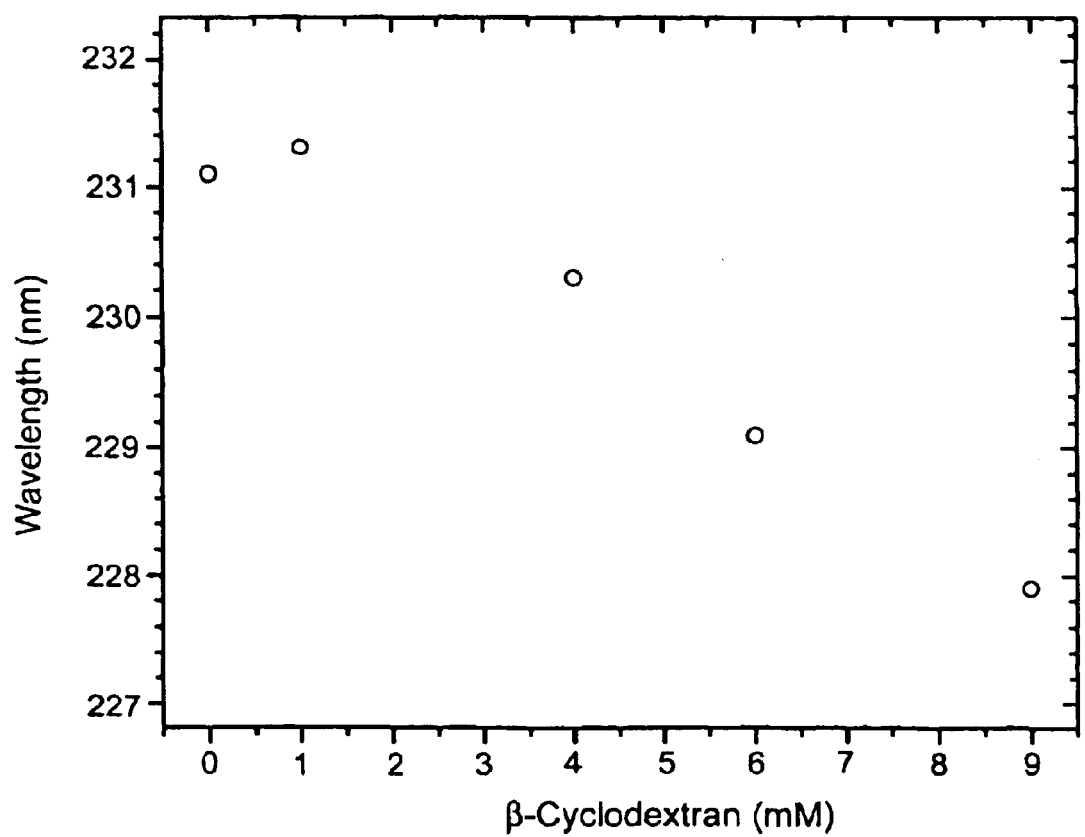
FIG. 1 is a plot of the hypsochromic shift observed with increasing concentrations of cyclodextrin. Artelinic acid concentration=10 mM.

The present invention is directed to a novel form of artemisinins that remain stable over time in solution. The artemisinins may be, but are not limited to artelinic acid and artesunic acid. This novel form of artemisinins uses a unique complexed form of the therapeutic agent with cyclodextrin analogs, such as but not limited to alpha-, beta-, and gamma-cyclodextrin analogs and their derivatives.

The present invention is directed to cyclodextrin complexed with artelinic acid in a 2:1 ratio which is a form of artemisinin that alters the electron cloud surrounding the artemisinin molecule in such a way as to stabilize this agent to promote bioavailability and membrane permeability while decreasing the likelihood of localized inflammation at the route of entry. Thus, this form of artemisinin increases its therapeutic activity. Artesunic acid was complexed with cyclodextrin, but in a unique 1:1 ratio in such a way as to stabilize the agent yield similar increases in its therapeutic activity.

The stability of the artemisinins is achieved by changing the physiocochemical properties such as but not limited to electron density, electrostatic potential and charge transfer mediated complexation.

The complexed cyclodextrin formulation of the artemisinins described deliberately shields the peroxide bridge of the artemisinin backbone from hydrolytic decomposition. Additionally, the aromatic benzoic acid portion of the artelinate molecule is also complexed with a second cyclodextrin molecule. This unique 2:1 complexation with cyclodextrin is not intuitively obvious because artelinic acid alone is unstable in aqueous solution. Simply placing cyclodextrin in solution with artelinic acid would not achieve these results, as the artelinic acid would not be in contact with the cyclodextrin to form complexation. Futher, cyclodextrin is know to form complexes with itself and thus may not be readily available in solution to interact efficiently and effectively with the artelinic acid. The inventors have placed artelinic acid and cyclodextrin into contact with one another and have complexed them in such a manner as to yield a stable 2:1 molecular species. The inventors have also placed artesunic acid and cyclodextrin into contact with one another and have complexed them in such a manner as to yield a stable 1:1 molecular species.

The present molecules are stable under ambient or physiologically relevant conditions.

Materials and Methods

β-cyclodextrin was obtained from Sigma-Aldrich Corp., St. Louis, Mo. Artelinic acid was alkalinized with NaOH to yield the sodium salt. Standardized PBS buffer at a pH of 7.4 was obtained from Invitrogen Corp., Carlsbad, Calif.

Absorption Spectroscopy Studies.

Mixtures of artelinate (10 μM) were prepared with increasing concentrations of β-cyclodextrin (0.0, 1.0, 4.0, 6.0, and 9.0 mM). Absorption spectra were collected on a Beckman DU Series 600 Spectrophotometer.

The spectra collected indicated a clear hypsochromic or blue shift in the absorption maximum at 230 nm with increasing concentrations of cyclodextrin. Hypochromic effects were also notable at 230 nm, as well as the broader transitions observed at 275 and 382 nm (FIG. 1). This combined observation is consistent with inclusion interactions of the benzoic anion of artelinate with cyclodextrin.

Figure 2A:
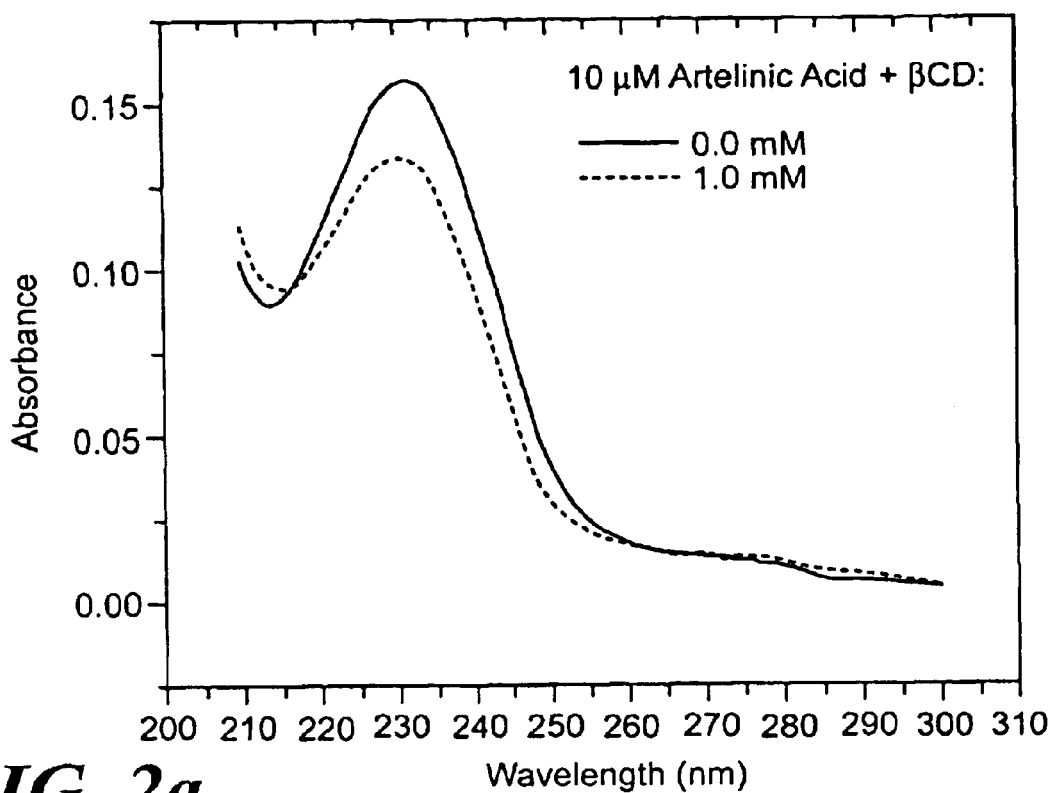
FIG. 2a is an absorption spectrum of 10 mM artelinic acid with and without 1 mM β-cyclodextrin.
Figure 2B:
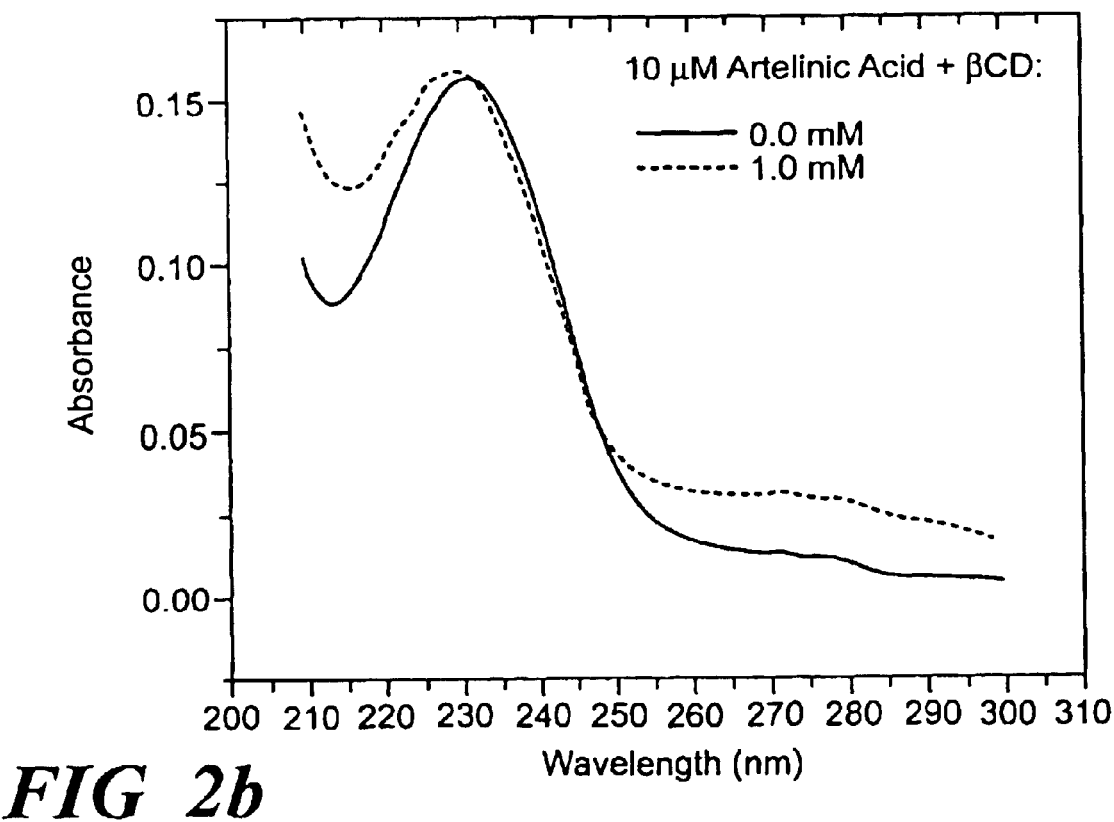
FIG. 2b is an absorption spectrum of 10 mM artelinic acid with and without 4 mM β-cyclodextrin.

Changes in observed isosbestic points at higher cyclodextrin concentrations indicates a complicated molecular species containing greater than a simple 1:1 molecular species (FIGS. 2a and 2b).

$^1$H NMR Studies.

Mixtures of β-cyclodextrin (2.5 mM) and artelinic acid (1.2 mM) were prepared in PBS (pH 7.4) and incubated at 37° C. for 2–3 hour to promote complexation prior to analysis.

All $^1$H NMR data was collected using a Bruker DRX-600 spectrometer operating at a proton frequency of 600.02 MHz at a temperature of 25° C. Solvent suppression was accomplished by application of the WATERGATE (WATER suppression by GrAdient Tailored Excitation) pulse sequence developed by Sklenar and co-workers. This sequence provides excellent suppression of the water resonance by a combination of rf pulses and a series of gradient pulses. The sequence combines a non-selective 90° pulse with a symmetrical echo formed by two short gradient pulses in conjunction with a 180 selective (on water) pulse train.

The two-dimensional WATERGATE-TOCSY experiment employed a modified MLEV-17 spin-lock sequence for a total mixing time of 80 ms, including the 2.5 ms trim pulses at the beginning and the end of the spin-lock. The spectrum was collected with a spectral width of 7183.91 Hz (11.972 ppm) using 2K data points with 32 scans per 256 $t_1$ increments with a 1.5 s recycle delay. The data was processed by multiplication with a 90° shifted sine-bell window function in each dimension, with one zero fill in the $f_1$ dimension before transformation to produce matrices consisting of 512 data points in both dimensions.

The two-dimensional WATERGATE-NOESY spectra were collected with a spectral width of 7183.91 Hz (11.972 ppm) using 2K data points with 128 scans per 512 $t_1$ increments with a 1.5 s recycle delay. The data was processed by multiplication with a 90° shifted sine-bell window function in each dimension, with one zero fill in the $f_1$ dimension before transformation to produce matrices consisting of 512 data points in both dimensions. Two different experiments were conducted with mixing times of 50 and 600 ms.

The two-dimensional WATERGATE-ROESY spectrum was collected with a spectral width of 7183.91 Hz (11.972 ppm) using 2K data points with 256 scans per 512 $t_1$ increments with a 1.5 s recycle delay with a spin-lock mixing pulse of 400 ms. The data was processed by multiplication with a 90° shifted sine-bell window function in each dimension, with one zero fill in the $f_1$ dimension before transformation to produce matrices consisting of 512 data points in both dimensions.

Figure 3:
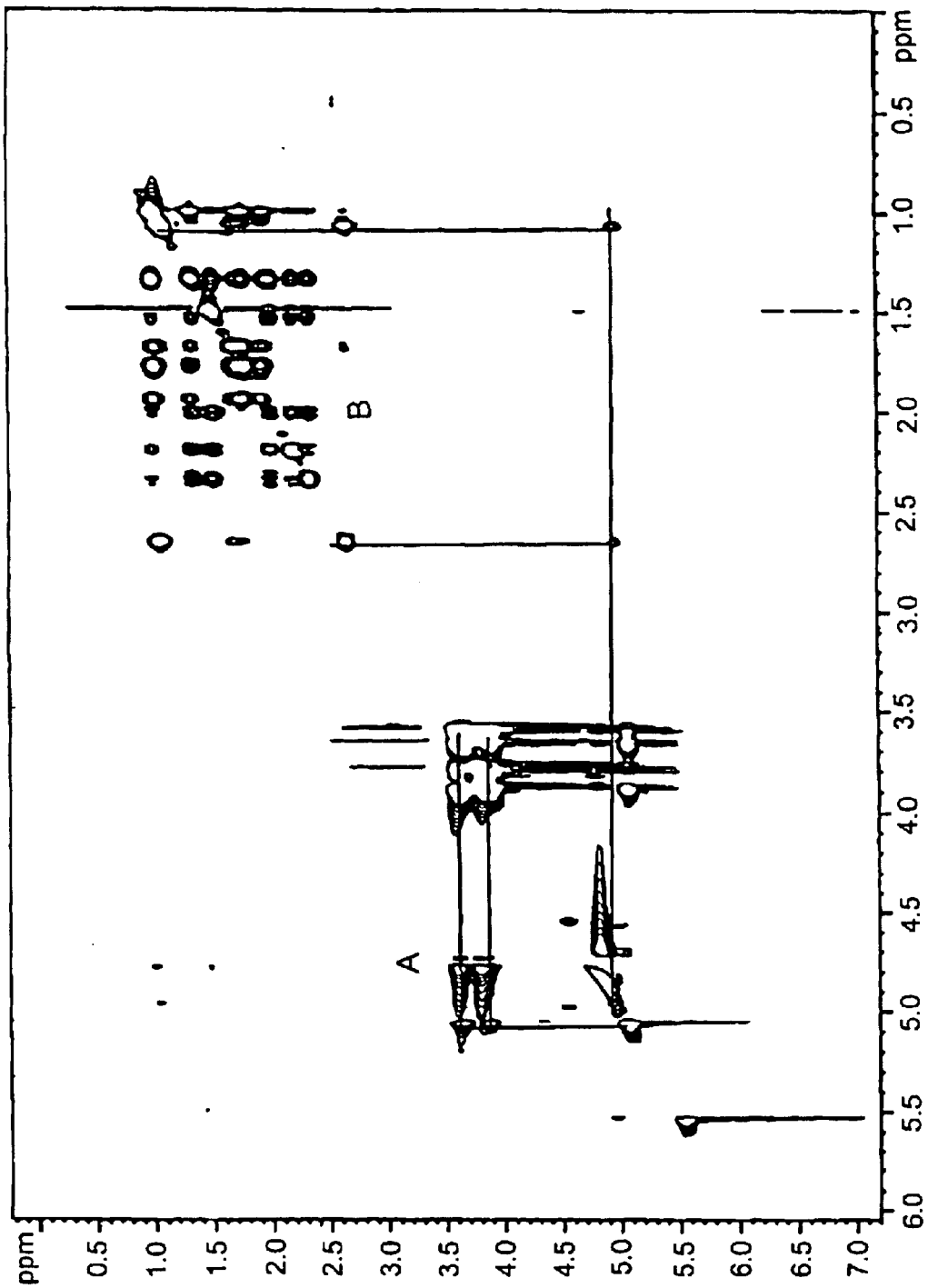
FIG. 3 is a 600 MHz WATERGATE-TOCSY NMR spectrum of 1.2 mM artelinic acid with 2.5 mM β-cyclodextrin in PBS (pH 7.4)
Figure 4:
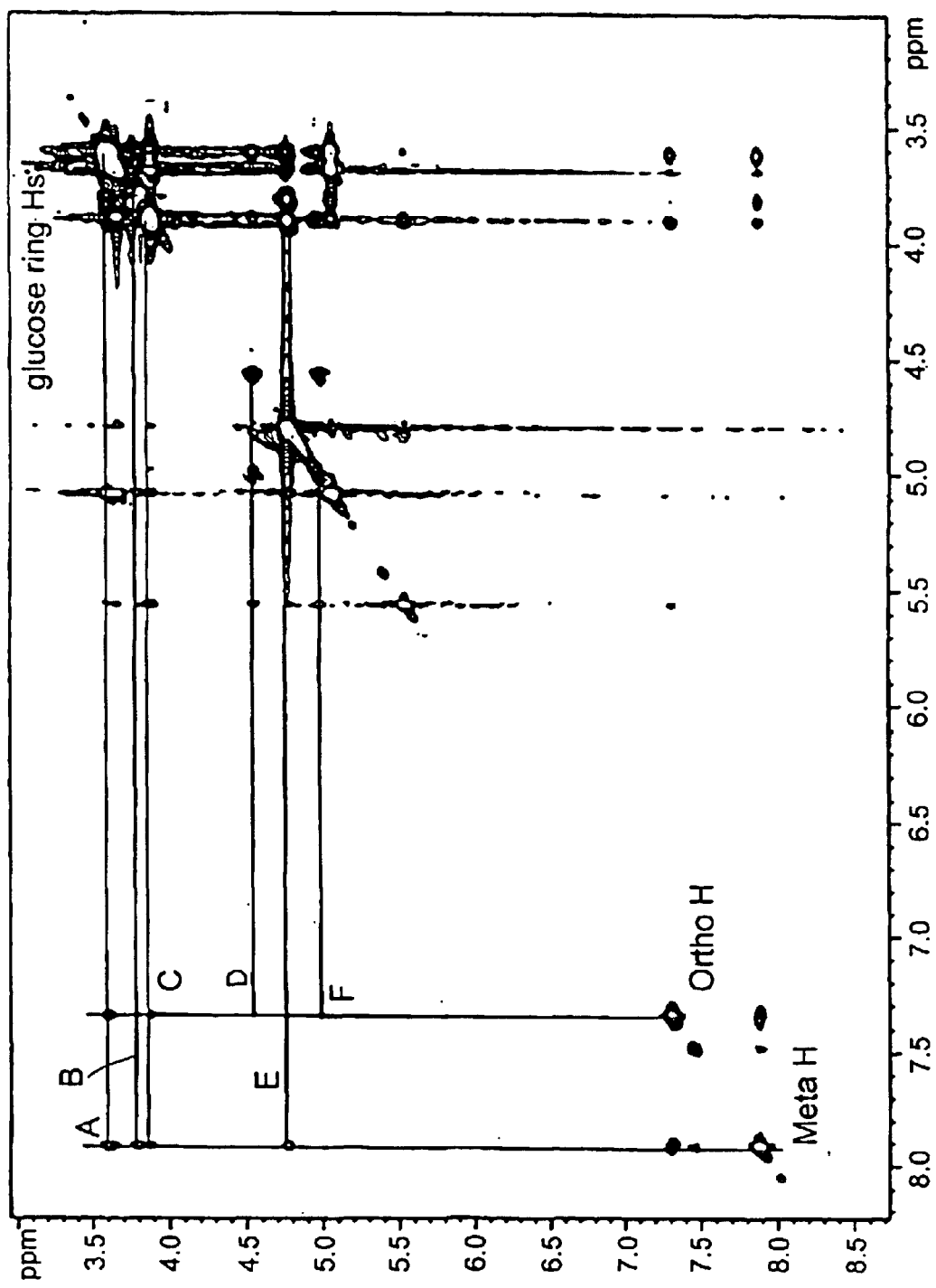
FIG. 4 is a 600 MHz WATERGATE-ROESY NMR spectrum of 1.2 mM artelinic acid with 2.5 mM β-cyclodextrin in PBS (pH 7.4)
Figure 5:
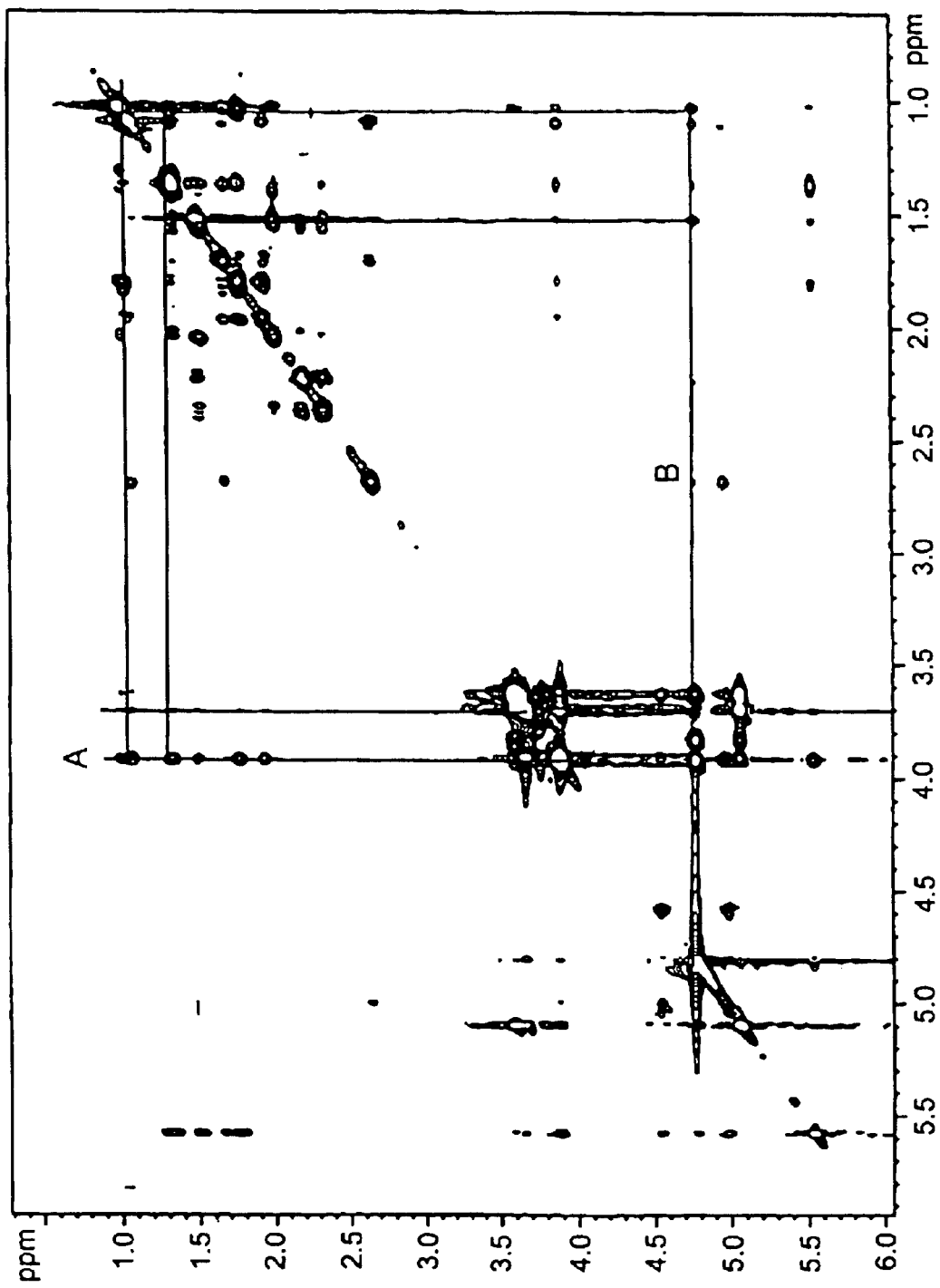
FIG. 5 is a 600 MHz WATERGATE-ROESY NMR spectrum of 1.2 mM artelinic acid with 2.5 mM β-cyclodextrin in PBS (pH 7.4)

Two-dimensional NMR methods were used to determine the degree of capping or complexation of artelinic acid by β-cyclodextrin. The 2D WATERGATE-TOSCY spectrum of artelinic acid (FIG. 3) clearly indicates that the individual spin-spin coupling networks of a mixture of artelinic acid and β-cyclodextrin can be resolved. In FIG. 3, the spin-spin coupling network for β-cyclodextrin is shown at A and the spin-spin coupling network for the alkyl ring of artenilate is shown at B. The 2D-rotating frame NOE spectrum, WATERGATE-ROESY, of artelinic acid was collected at a mixing time of 400 ms and is shown in FIG. 4. The labeled intermolecular ROE interaction between the aromatic protons of artelinic acid with both the anomeric and ring protons of β-cyclodextrin proves that this region of artelinic acid is complexed with one molecule of β-cyclodextrin. In FIGS. 4, A, B and C indicate the intermolecular dipolar ROE coupling between the aromatic protons of artelinate with the glucose ring protons of β-cyclodextrin. The ROE between the meta protons are more intense than those observed for the ortho protons indicating that meta protons are inserted deeper into the cavity. D and F indicate the dipolar coupling between the ortho protons of artelinate with the two benzyl protons of artelinate. E indicates the dipolar coupling between the meta protons of artelinate with the anomeric protons of β-cyclodextrin. FIG. 5 shows the alkyl region of this same spectrum. The labeled intermolecular ROE's between the alkyl ring protons of artelinic acid with both the anomeric and ring protons of β-cyclodextrin indicate that this region of artelinic acid is complexed with one molecule of β-cyclodextrin. These observations are similar to those reported by Nishijo (Nishijo, J.; Nagai, M.; Yasuda, M.; Ohno, E.; Ushiroda, Y. *J. Pharm. Sci.* 1995, 84, 1420–1426) and by Redenti (Redenti, E.; Ventura, P.; Fronza, G.; Selva, A.; Rivara, S.; Plazzi, P. V.; Mor, M. *J. Pharm. Sci.* 1999, 88, 599–607) in similar NMR β-cyclodextrin complexation studies. In FIG. 5, A represents a region that contains the dipolar coupling between the ring protons of β-cyclodextrin and the alkyl ring proton of artelinate; and B represents the region that contains the dipolar coupling of the anomeric protons of β-cyclodextrin with the alkyl protons of artelinate.

Two 2D WATERGATE-NOESY spectra were collected at mixing times of 50 and 600 ms (data not shown). The NOESY spectrum collected at 600 ms gave similar intermolecular and intramolecular NOE's to those observed in the ROESY spectrum, however the observed intensities were reduced. The NOESY spectrum collected at 50 ms did not exhibit the intermolecular NOE's between artenilate and β-cyclodextrin. This observation is consistent with what one would expect due to the fact that intermolecular NOE's require a longer mixing time to develop as compared to intramolecular NOE's.

The 2D ROESY and NOESY data clearly indicate that both the alkyl and aromatic regions of artelinic acid are complexed with one individual molecule of β-cyclodextrin.

Figure 6:
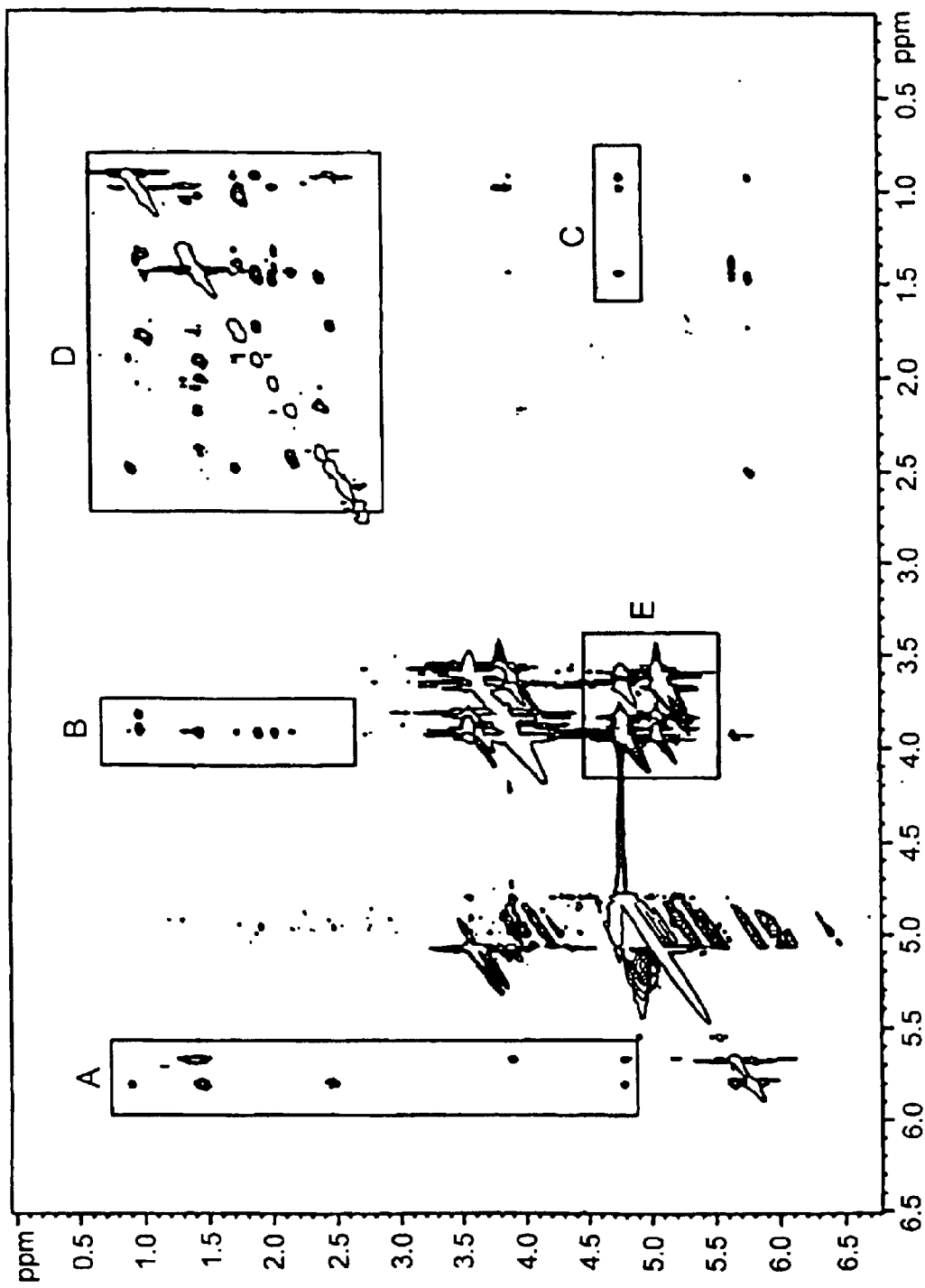
FIG. 6 is a 600 MHz WATERGATE-ROESY NMR spectrum of artesunate with an excess of β-cyclodextrin in PBS (pH 7.4)

In FIG. 6, the spectrum of artesunate with an excess of β-cyclodextrin in PBS is shown. This data clearly indicates that the artesunate is capped by β-cyclodextrin in a 1:1 ratio. The region that is represented by A contains the intramolecular dipolar coupling the alkyl ring proton of artesunate. The region that is represented by B contains the intermolecular dipolar coupling the alkyl ring proton of artesunate with the ring protons of β-cyclodextrin. The region that is represented by C contains the intermolecular dipolar coupling the alkyl ring proton of artesunate with the anomeric protons of β-cyclodextrin. The region that is represented by D contains additional intramolecular dipolar coupling the alkyl ring proton of artesunate. The region that is represented by E contains the intramolecular dipolar coupling of the β-cyclodextrin.

Figure 7A:
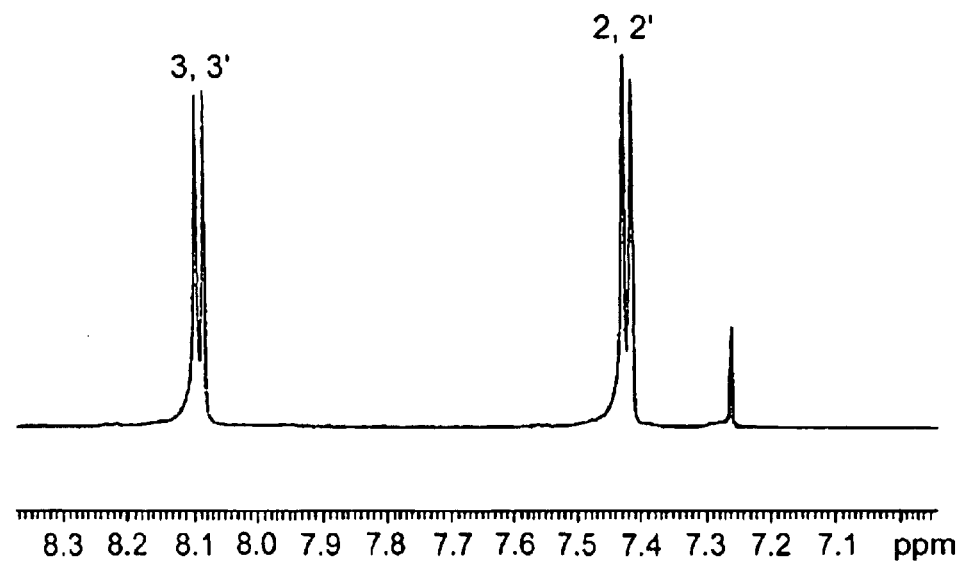
FIG. 7a is the aromatic region of the 600 MHz proton spectra of 1.2 mM artelinic acid.
Figure 7B:
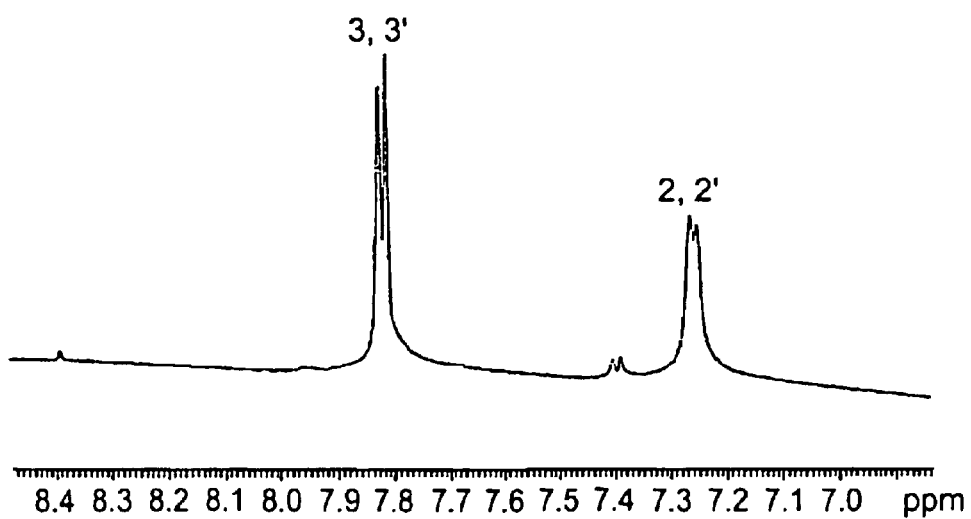
FIG. 7b is the aromatic region of the 600 MHz proton spectra of 1.2 mM artelinic acid complexed with 2.5 mM β-cyclodextrin in PBS (pH 7.4)

FIG. 7a shows the aromatic region of the 600 MHz proton spectra of 1.2 mM artelinic acid and FIG. 7b is the aromatic region of the 600 MHz proton spectra of 1.2 mM artelinic acid complexed with 2.5 mM β-cyclodextrin. Upon complexation the aromatic resonances of artelinate are both shifted upfield. The chemical shift values and the relative changes in chemical shift values are given in Table 1. A similar shift of aromatic protons resonances of ketoconazole on complexation with β-cyclodextrin was reported by Redenti and co-workers (Redenti, E.; Ventura, P.; Fronza, G.; Selva, A.;Rivara, S.; Plazzi, P. V.; Mor, M. *J. Pharm. Sci.* 1999, 88, 599–607). In addition, the intensity of the resonance for protons 2 and 2' is reduced indicating complexation.

TABLE 1

$^1$H Chemical Shift Assignments (δ) for the Aromatic Protons and Methyl Protons of Artelinic Acid

| Proton | Chemical Shift | Chemical Shift complexed with β-cyclodextrin | Δδ (ppm) |
|---|---|---|---|
| 3 and 3' | 8.09 | 7.82 | +0.27 |
| 2 and 2' | 7.42 | 7.25 | +0.17 |
| methyl #1 | 0.98 | 1.02 | −0.04 |
| methyl #2 | 0.95 | 0.95 | 0.00 |

Figure 8A:
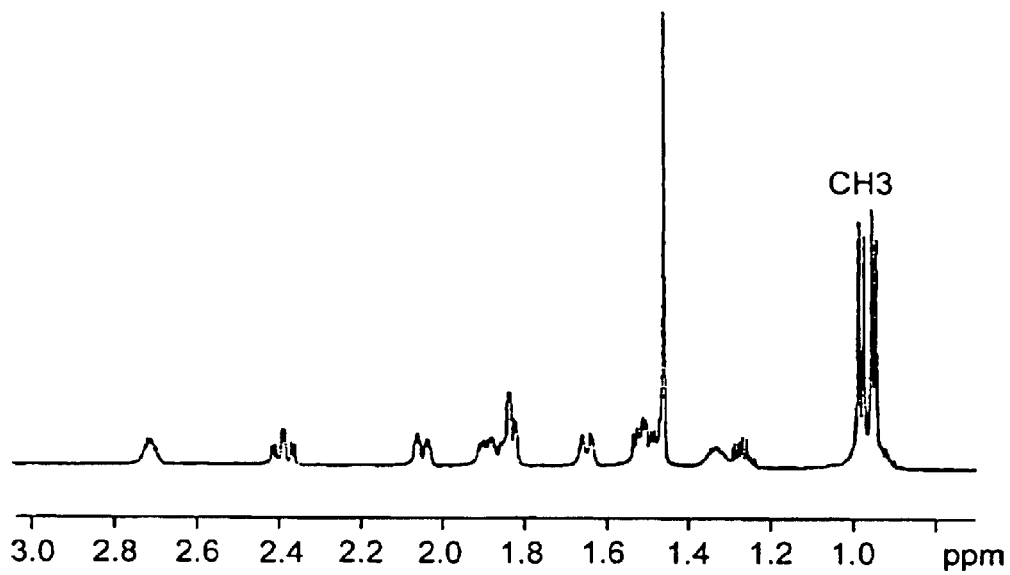
FIG. 8a is the alkyl region of the 600 MHz proton NMR spectra of 1.2 mM artelinic acid.
Figure 8B:
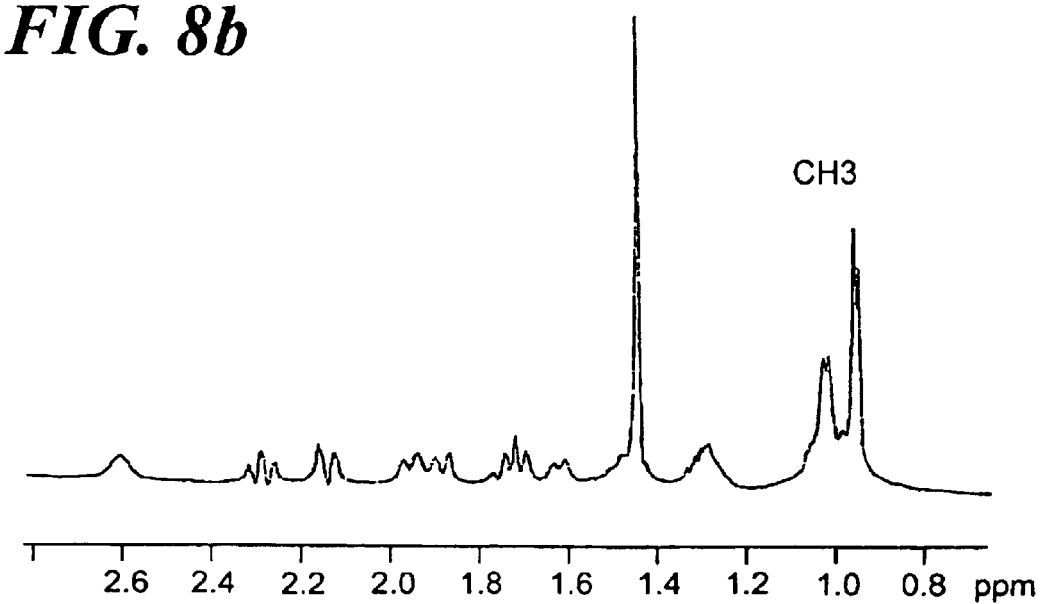
FIG. 8b is a 600 mHz proton NMR spectrum of 1.2 mM artelinic acid complexed with 2.5 mM β-cyclodextrin in PBS (pH 7.4)

FIG. 8a shows the alkyl region of the 600 MHz proton spectra of 1.2 mM artelinic acid and FIG. 8b shows 1.2 mM artelinic acid complexed with 2.5 mM β-cyclodextrin. As seen from these spectra the chemical shift position and the appearance of the methyl protons have changed indicating complexation of this region of the molecule with β-cyclodextrin. The chemical shift of the resonances for methyl group #1 are shifted upfield by 0.04 ppm (Table 1). The resonances for both methyl groups were broadened and less well resolved.

Figure 9A:
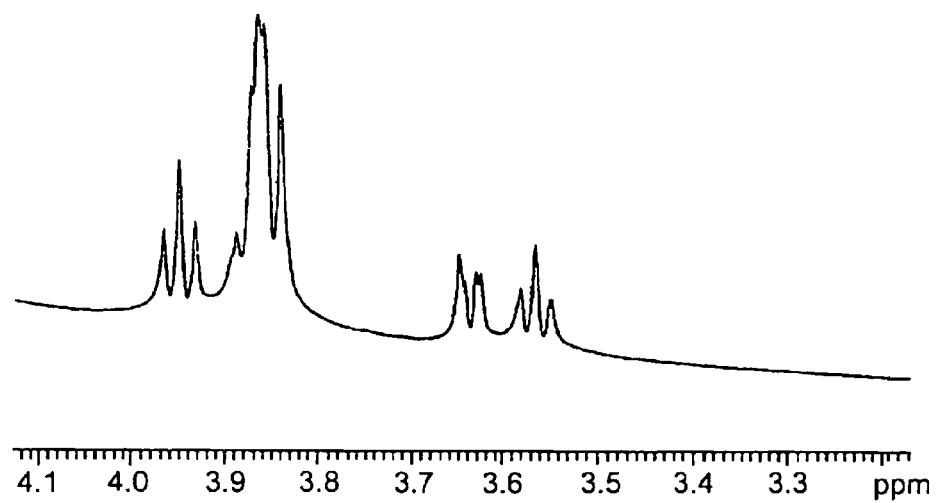
FIG. 9a is a 600 MHz proton NMR spectrum of 2.5 mM β-cyclodextrin in PBS (pH 7.4)
Figure 9B:
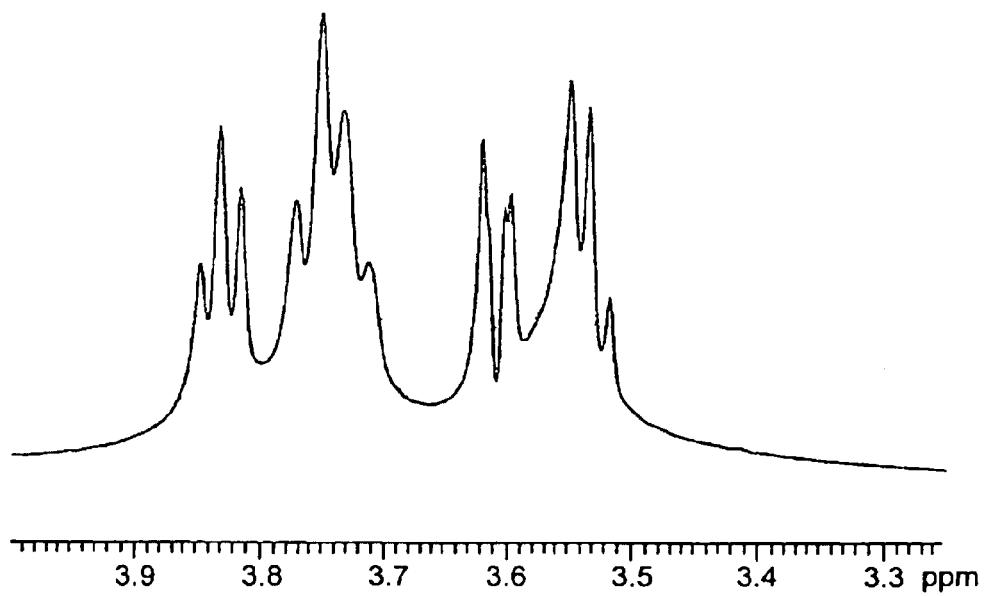
FIG. 9b is a 600 MHz proton NMR spectrum of 2.5 mM β-cyclodextrin with 1.2 mM artelinic acid in PBS (pH 7.4)

FIG. 9a is a 600 MHz proton spectra of 2.5 mM β-cyclodextrin and FIG. 9b is a 600 MHz proton spectra of 2.5 mM β-cyclodextrin with 1.2 mM artelinic acid. These spectra clearly indicate that chemical values for protons 2 to 6 on β-cyclodextrin change on complexation with artelinic acid. Similar shifts in the proton resonances for β-cyclodextrin have been reported by Nishijo and co-workers (Nishijo, J.; Nagai, M.; Yasuda, M.; Ohno, E.; Ushiroda, Y. *J. Pharm. Sci.* 1995, 84, 1420–1426).

Figure 10A:
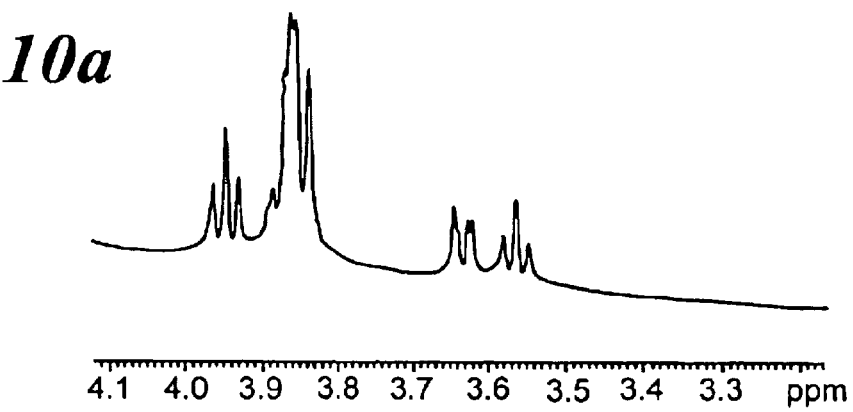
FIG. 10a is a 600 MHz proton NMR spectrum (protons number 2 to 6) of 2.5 mM β-cyclodextrin in PBS (pH 7.4)
Figure 10B:
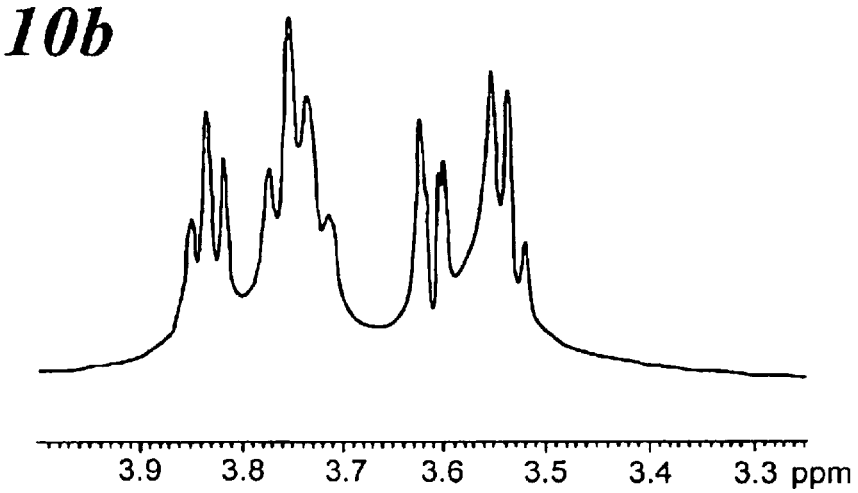
FIG. 10b is a 600 MHz proton NMR spectrum (protons number 2 to 6) of 2.5 mM β-cyclodextrin complexed with 1.2 mM artelinic acid in PBS (pH 7.4)
Figure 10C:
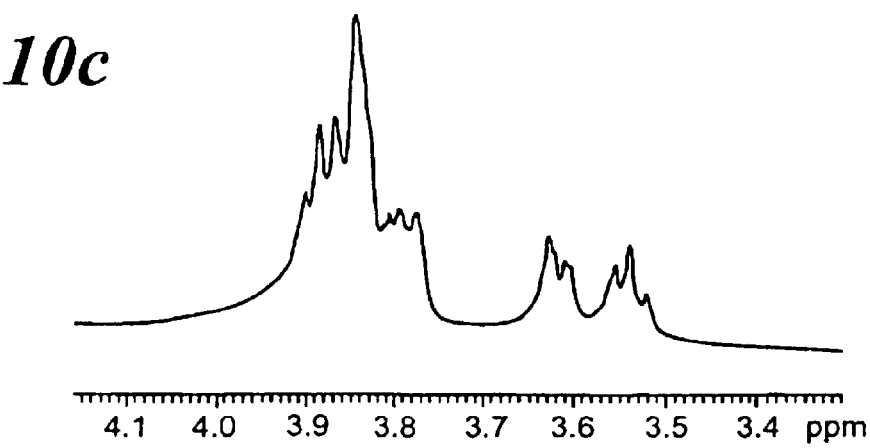
FIG. 10c is a 600 MHz proton NMR spectrum (protons number 2 to 6) of artesunate with an excess of β-cyclodextrin in PBS (pH 7.4)
Figure 11:
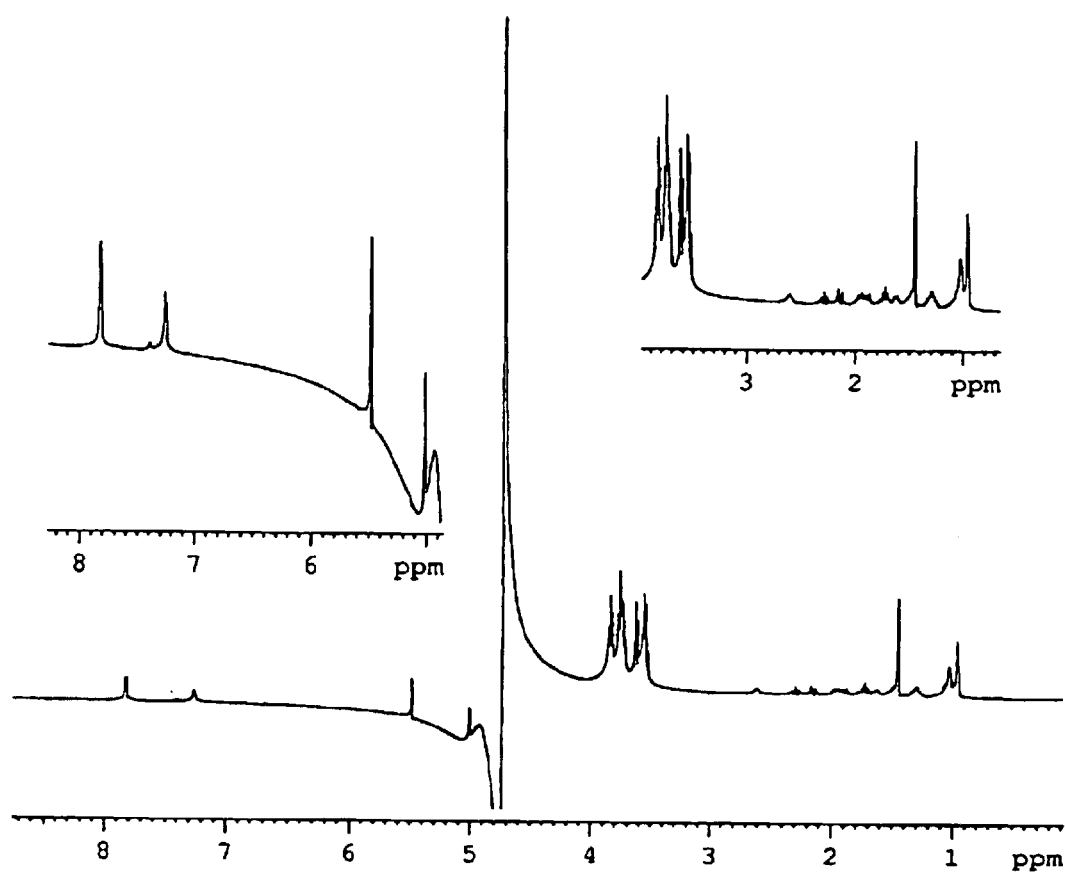
FIG. 11 is a 600 MHz proton NMR spectrum of 2.5 mM β-cyclodextrin and 1.2 mM artelinic acid in PBS buffer at pH 7.4 with 1:9 $D_2O/H_2O$.
Figure 12:
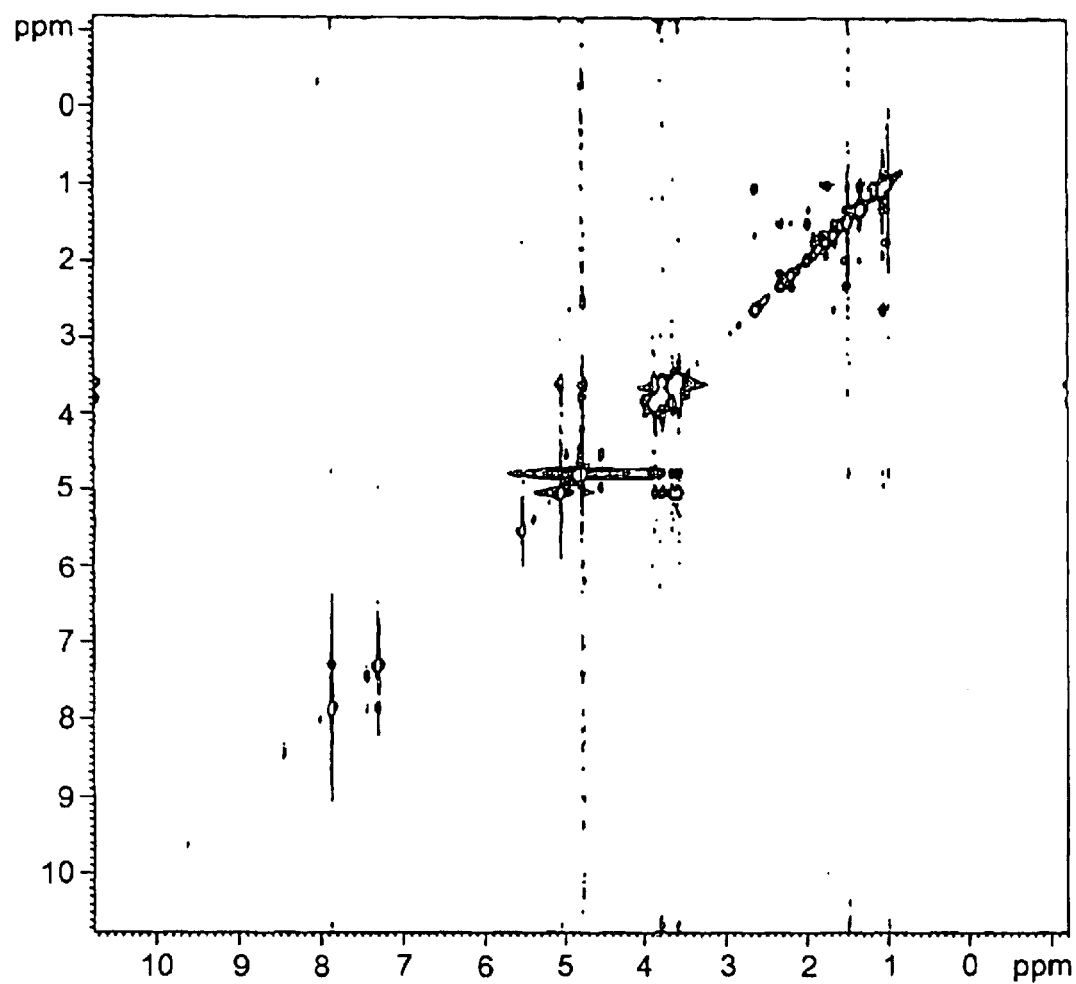
FIG. 12 is a 2D NOESY spectrum of 2.5 mM β-cyclodextrin and 1.2 mM artelinic acid in PBS buffer at pH 7.4 with 1:9 $D_2O/H_2O$.
Figure 13:
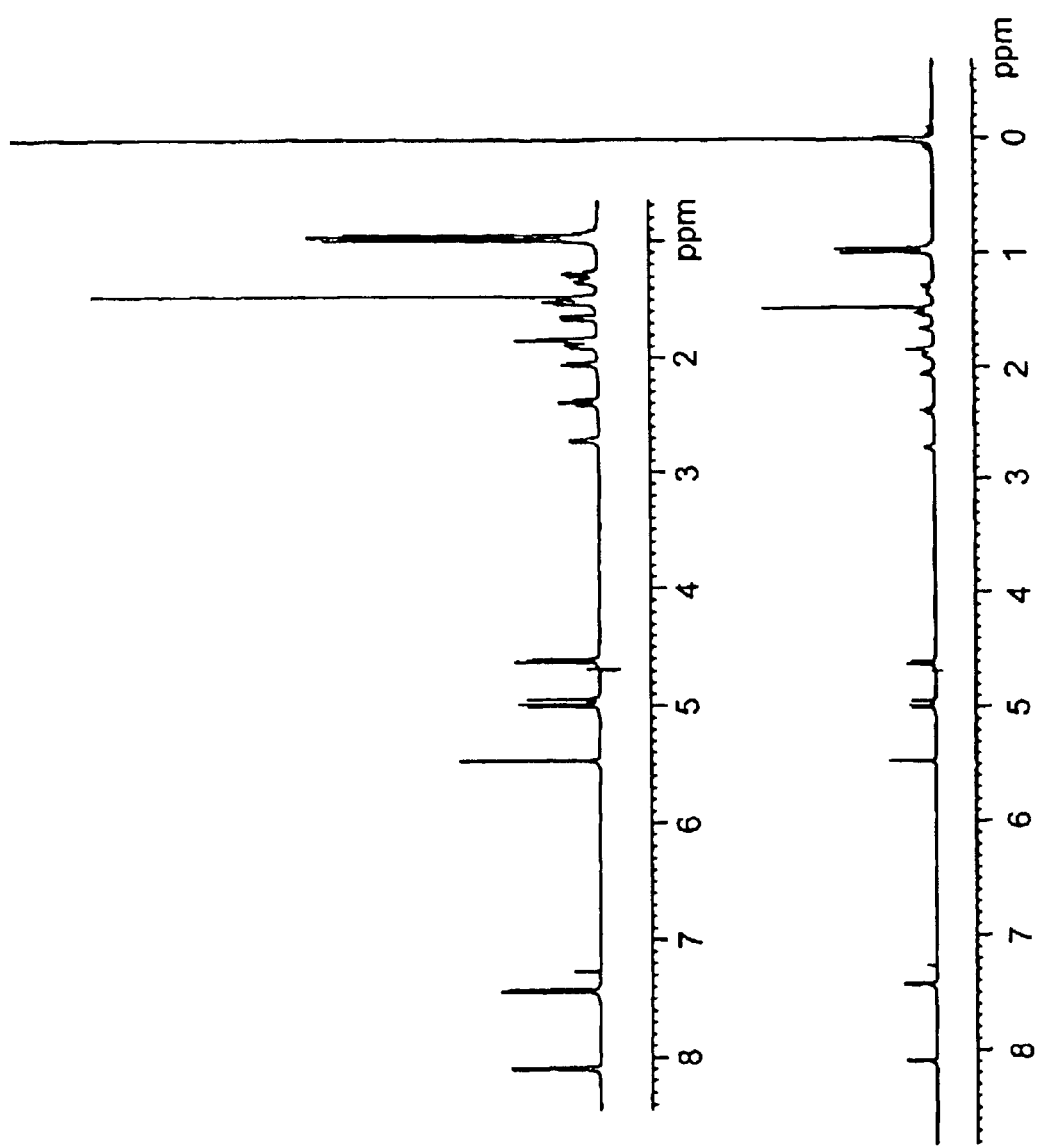
FIG. 13 is a 600 MHz proton NMR spectrum of artelinic acid BN BP11387, WR# 255663.
Figure 14:
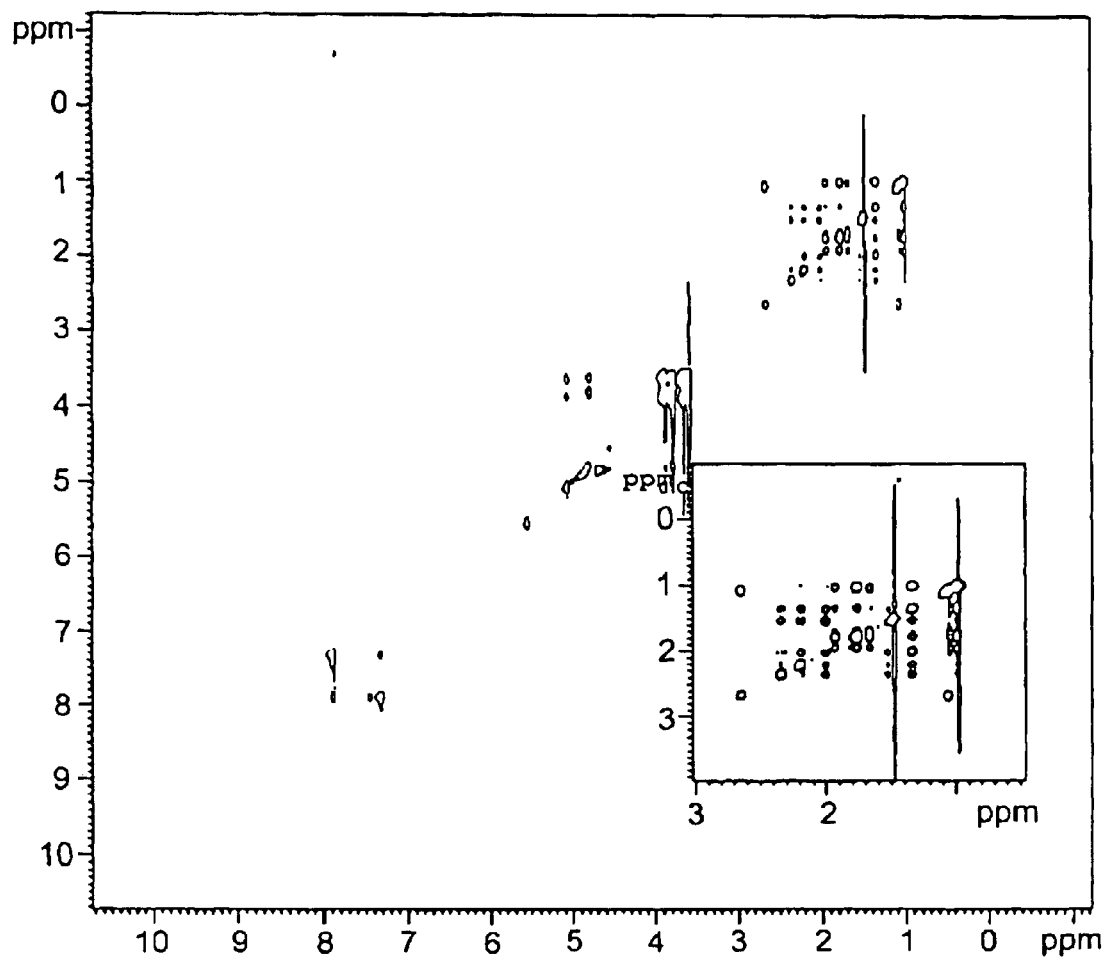
FIG. 14 is a 600 MHz proton NMR spectrum of 2D TOESY spectrum of 2.5 mM β-cyclodextrin and 1.2 mM artelinic acid in PBS buffer at pH 7.4 with 1:9 $D_2O/H_2O$.
Figure 15:
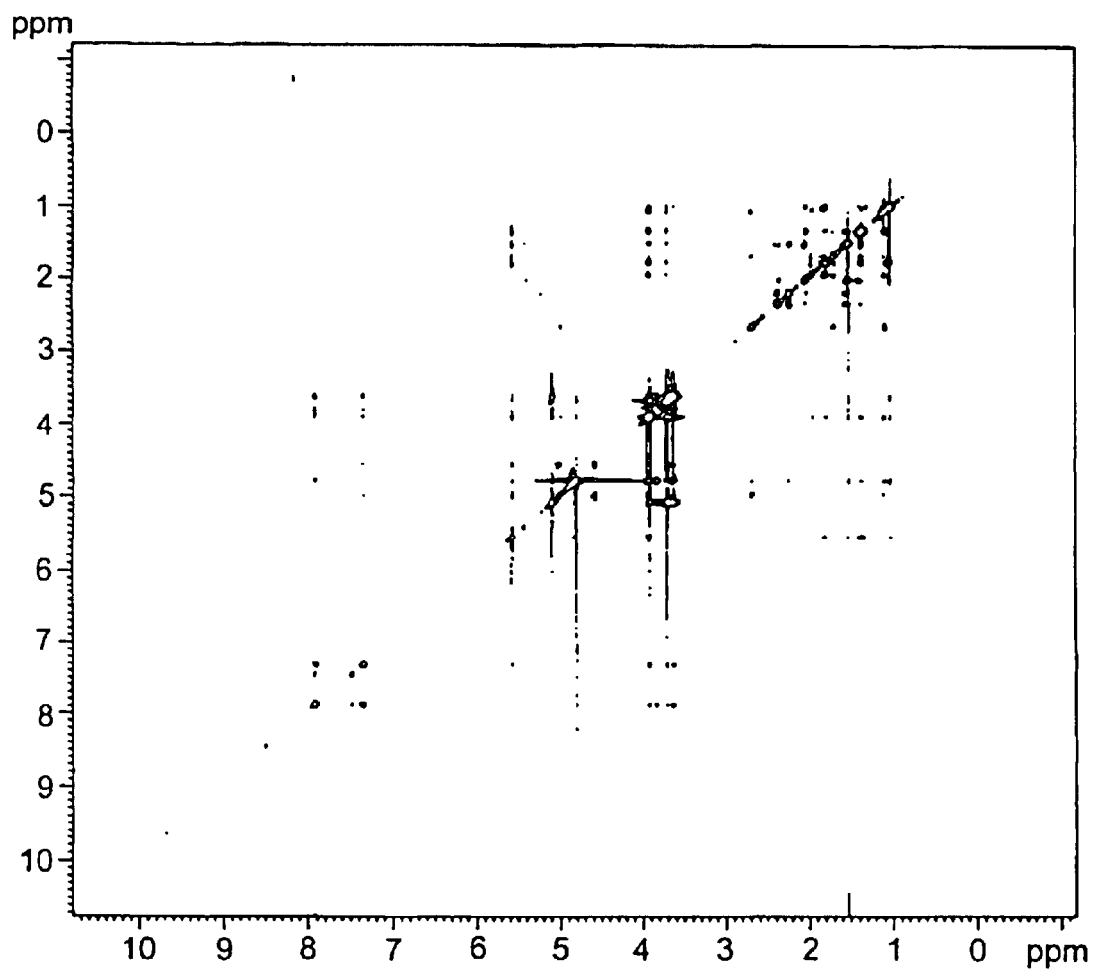
FIG. 15 is a 600 MHz proton NMR spectrum of 2D ROESY spectrum of 2.5 mM β-cyclodextrin and 1.2 mM artelinic acid in PBS buffer at pH 7.4 with 1:9 $D_2O/H_2O$.
Figure 16:
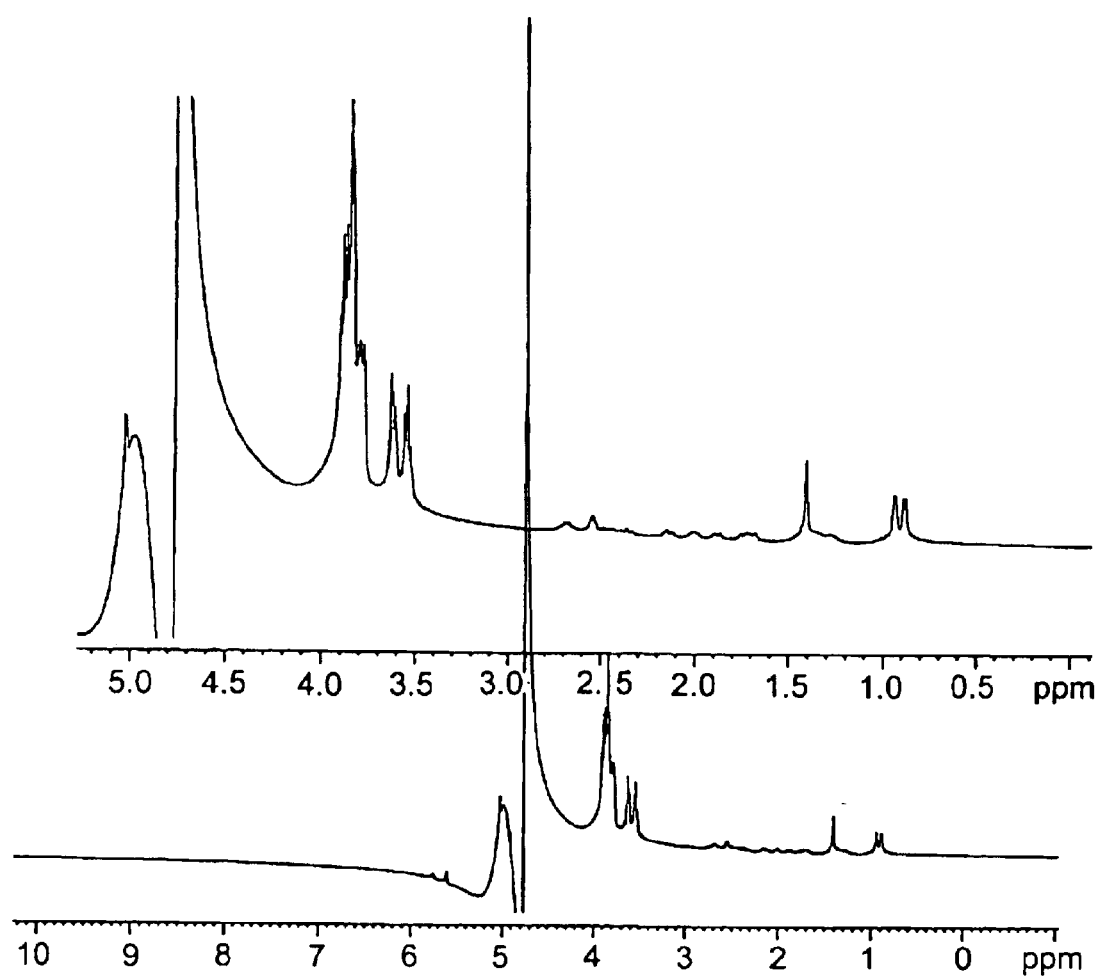
FIG. 16 is a 600 MHz proton NMR spectrum of artesunate with an excess of β-cyclodextrin in PBS buffer at pH 7.4.
Figure 17:
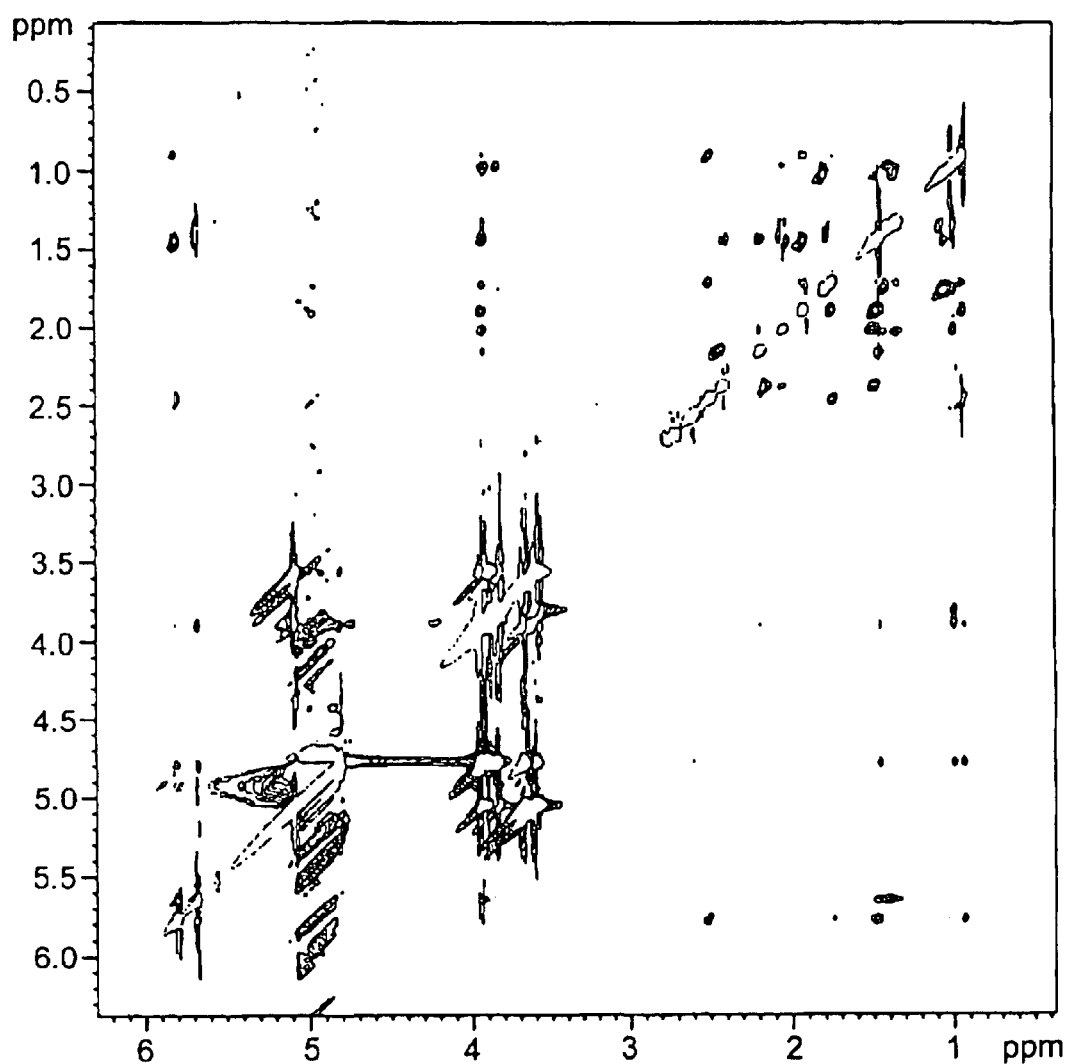
FIG. 17 is a 600 MHz proton NMR spectrum of 2D ROESY spectrum of artesunate with an excess of β-cyclodextrin in PBS buffer at pH 7.4.

FIGS. 10a–10c show the proton spectra (protons number 2 to 6) of 2.5 mM β-cyclodextrin, 2.5 mM β-cyclodextrin complexed with 1.2 mM artelinic acid and 1.2 mM artesunate in an excess of β-cyclodextrin, respectively. These spectra clearly indicate a different mode of complexation for the two artemisinin analogs.

Table 2 summarizes the chemical shift assignments for cyclodextrin compared with the corresponding complexes with artelinic acid and artesunic acid as derived from FIGS. 9 and 10. The change in chemical shifts (Δδ) clearly demonstrate that both cyclodextrins of the artelinic acid complex and the cyclodextrin of the artesunic acid complex coordinate at the 3-H end or secondary face (FIG. 18) of the cyclodextrin. Further, the benzoic acid moiety of artelinic acid coordinates deeply into the cyclodextrin pocket yielding significant changes in chemical shift for the 3-H, 5-H, and 6-H protons. In contrast, artesunic acid, which only binds to one cyclodextrin at the peroxide bridge, produced chemical shift changes of a lower magnitude indicating a more shallow binding interaction. Lastly, for the artesunate-cyclodextrin complex the changes in chemical shift indicate Δδ of 6H<5H<3H which clearly demonstrates this shallow binding interaction compared to the deep insertion of the benzoic acid moiety of artelinic acid. This data clearly supports a unique stereochemical arrangement based upon the physicochemical properties of each molecular species to yield a specific stable complex.

TABLE 2

$^1$H Chemical Shift Assignments (δ) for the Cyclodextrin Protons (2 through 6)

|  | 2H | 3H | 4H | 5H | 6H |
|---|---|---|---|---|---|
| β-cyclodextrin | 3.63 | 3.94 | 3.56 | 3.83 | 3.86 |
| artelinic acid | 3.61 | 3.83 | 3.53 | 3.72 | 3.74 |
| Δδ | 0.02 | 0.11 | 0.03 | 0.11 | 0.12 |
| β-cyclodextrin | 3.63 | 3.94 | 3.56 | 3.83 | 3.86 |
| artesuate | 3.62 | 3.88 | 3.55 | 3.79 | 3.84 |
| Δδ | 0.01 | 0.06 | 0.01 | 0.04 | 0.02 |

FIGS. 11 through 17 provide ancillary and supportive data that was used in elucidating the structural conformation of the described cyclodextrin complexes.

Molecular Electrostatic Potential Mapping and Docking/Affinity Determinations.

Molecular Electrostatic Potential (MEP) maps on cyclodextrin and artelinic acid were developed by calculating electrostatic potentials on the van der Waals surface of the molecules using the semi-empirical PM3 molecular orbital theory as implemented in the SPARTAN software (SPARTAN version 4.0, Wavefunction, Inc., 18401 Von Karman Ave., #370, Irvine, Calif. 92715 U.S.A. 1995 Wavefuntion, Inc.). PM3 is a semi-empirical quantum chemical theory model based on Thiel's integral formalism underlying MNDO/d, and is used in conjunction with parameters for both transition and non-transition metals (reference: (a) W. Thiel and A. Voityuk, *Theor. Chim. Acta.*, 81, 391, (1992); (b) W. Thiel and A. Voityuk, *Int. J. Quantum Chem.*, 44, 807 (1992).

Molecular electrostatic potential (MEP) maps and their electrostatic potential energy isopotential profiles were generated and sampled over the entire accessible surface of a molecule (corresponding roughly to a van der Waals contact surface). The MEP maps provide a measure of charge distribution from the point of view of an approaching reagent. This is calculated using a test positive charge as the probe. Thus, these types of profiles can provide an estimate of electronic distribution surrounding the molecule so as to enable qualitative assessment of any possible interaction with an approaching molecule. However, conformation search calculations using the "systematic search" technique via the single-point PM3 method of SPARTAN were used to generate different conformers for each of the molecules. The minimum energy conformer with highest abundance (a Boltzman population density greater than 70.0%) was chosen for full geometry optimization using the PM3 algorithm. The MEP profiles were generated on the optimized geometry of the molecules. The computations were carried out on a Silicon Graphics Octane workstation.

To further understand the binding affinities between cyclodextrin and artelinic acid, the complete optimized structures of both the compounds have been considered and docking calculations using the Docking/affinity module in Insight II (Accelrys Inc., 9685 Scranton Road, San Diego, Calif. 92121-3752) were conducted. See Oprea, T. I. and Marshall, G. R. (1998) Receptor-based prediction of binding affinities. Perspectives in Drug Discovery and Design 9/10/11:35–61; and Insight II User Guide, San Diego: Accelrys Inc. (2002), which are herein incorporated by reference.

Docking/affinity module in Insight II allows calculating the nonbonded energy between two molecules using explicit van der Waals energy, explicit electrostatic (Coulombic) energy, or both van der Waals and electrostatic energies. The number of atoms included in the calculation can be limited by specifying a monomer- or residue-based cutoff. Other methods known in the art may be used, for example, the computation can be done using a pre-computed energy grid.

Figure 18A:
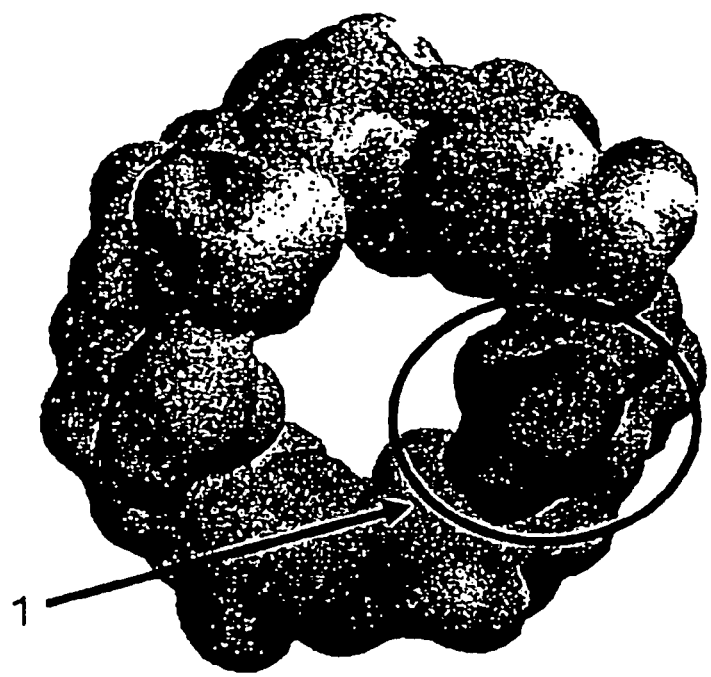
FIG. 18a is the electrostatic potential map of the primary face of β-cyclodextrin looking into the molecule from the top.
Figure 18B:
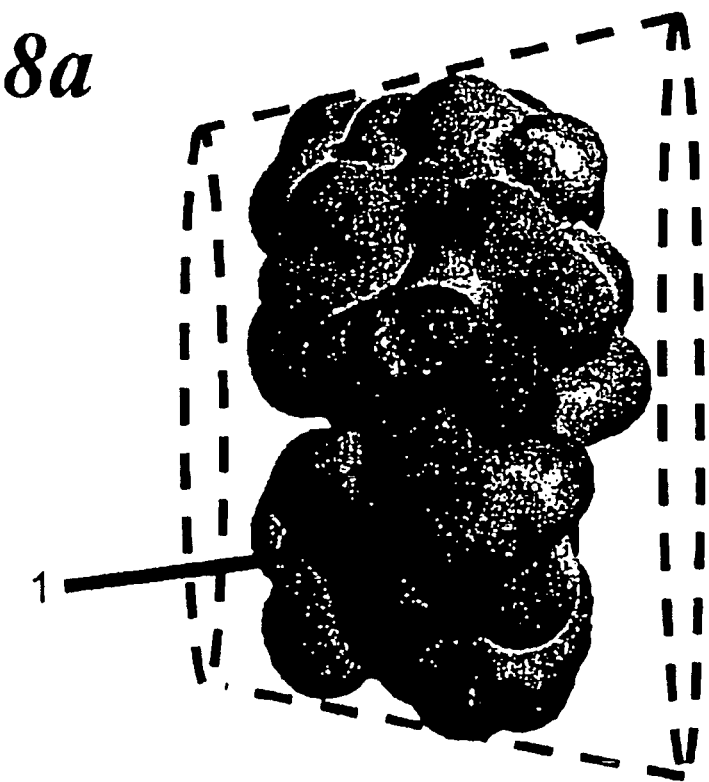
FIG. 18b is the electrostatic potential map of the primary face of β-cyclodextrin as shown in FIG. 18a rotated to the left.
Figure 18C:
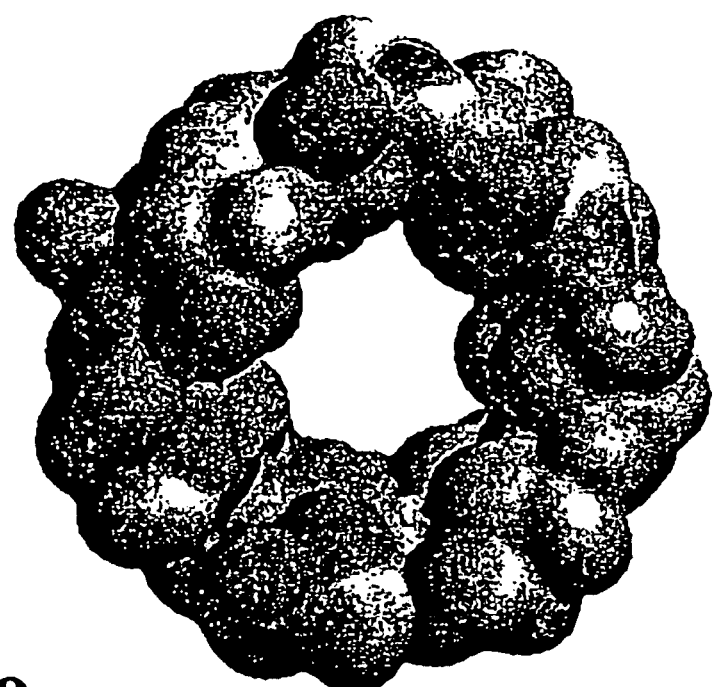
FIG. 18c is the electrostatic potential map of the secondary face of β-cyclodextrin.
Figure 18D:
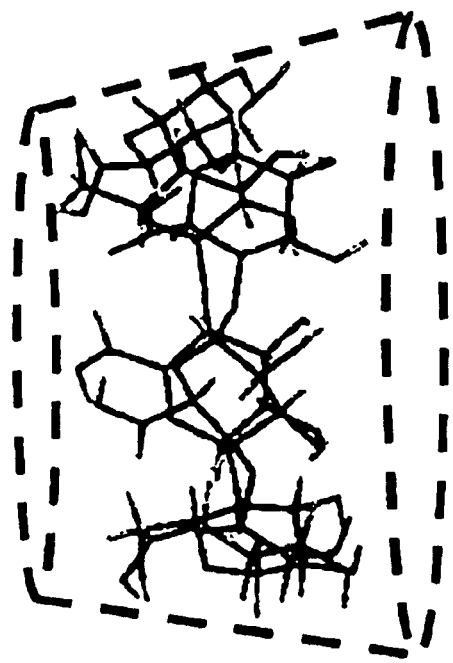
FIG. 18d is a molecular model of FIG. 18d illustrating the positions of specific atoms.

These molecular modeling determinations based on unique and specific physicochemical properties of the artemisinins studied complexed with β-cyclodextrin produced conceptual models which clearly rationalized the direct physical measurements of the NMR experiments. FIGS. 18a–d illustrate the unique electrostatic potential map of β-cyclodextrin showing the primary binding faces (FIGS. 18a and 18b) and secondary binding faces (FIG. 18c and FIG. 18d). Most notable is the unique net positive region 1 of the electron cloud at the primary face.

Figure 19A:
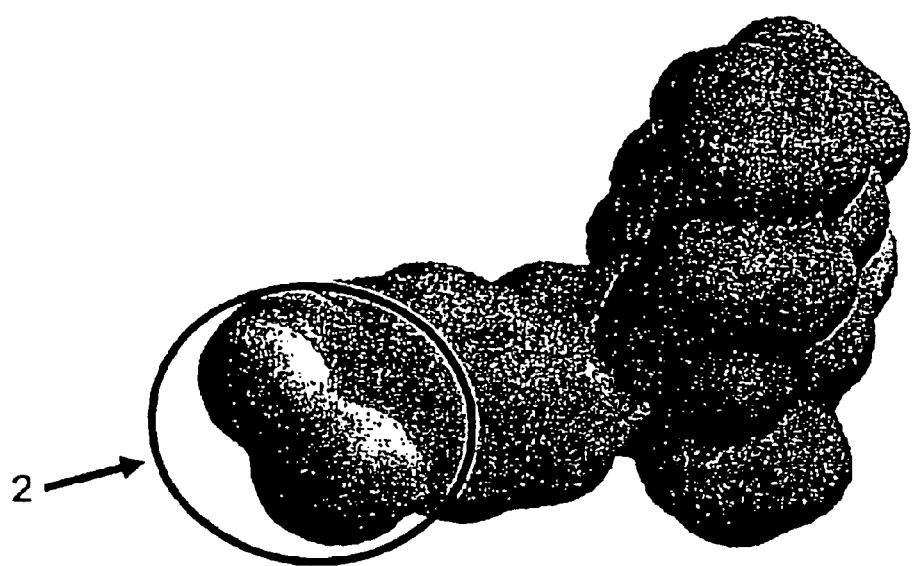
FIG. 19a is a side view of the electrostatic potential map of artelinic acid.
Figure 19B:
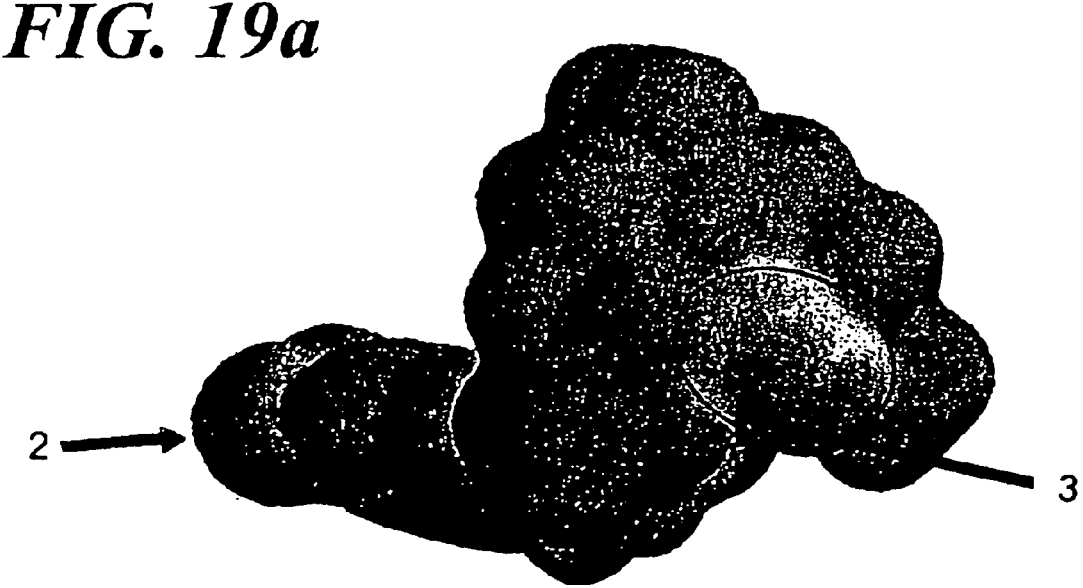
FIG. 19b is a rear view of the electrostatic potential map of artelinic acid.

FIGS. 19a and 19b illustrate the unique electrostatic potential map of artelinic acid. Most notable is the dense negative region 2 of the carboxylic acid tail as well as a more subtle negative region 3 of the peroxide bridge.

Figure 20:
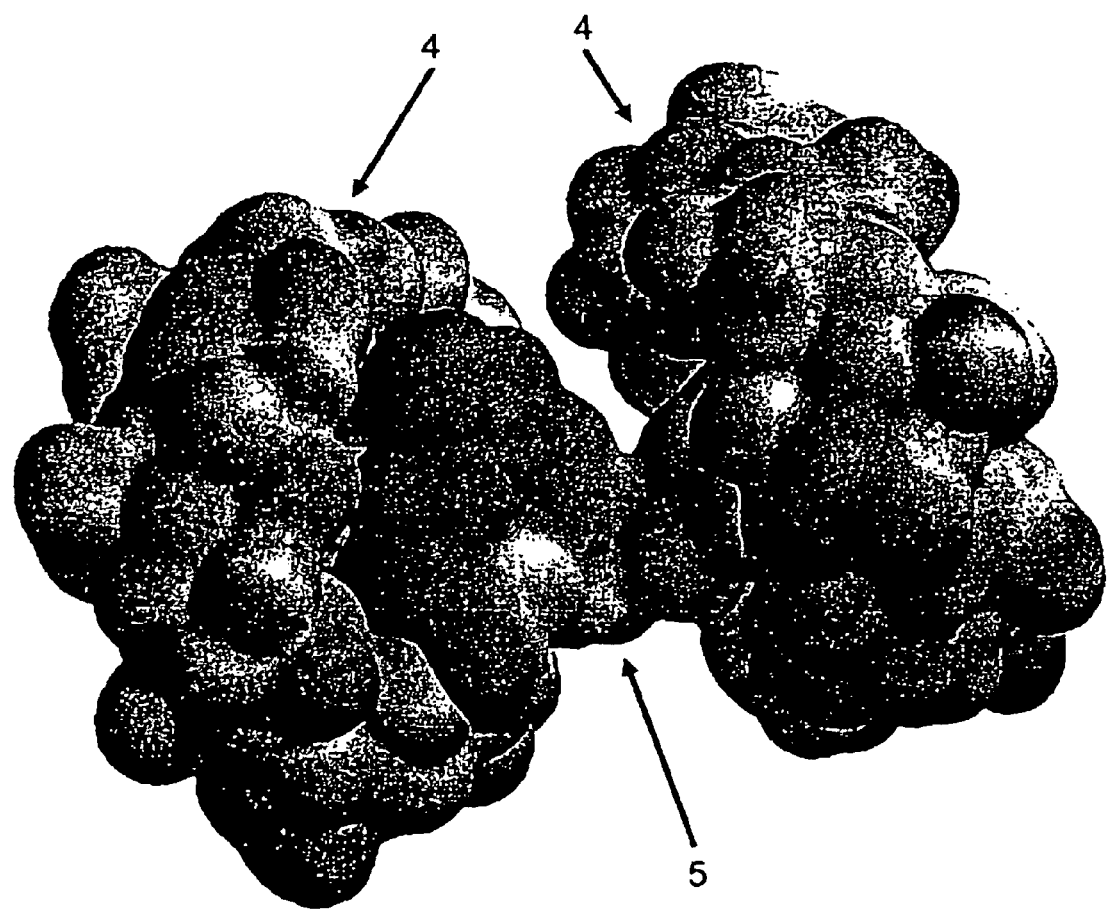
FIG. 20 is the electrostatic potential map of β-cyclodextrin complexed with artelinic acid in a 2:1 molecular ratio.
Figure 21:
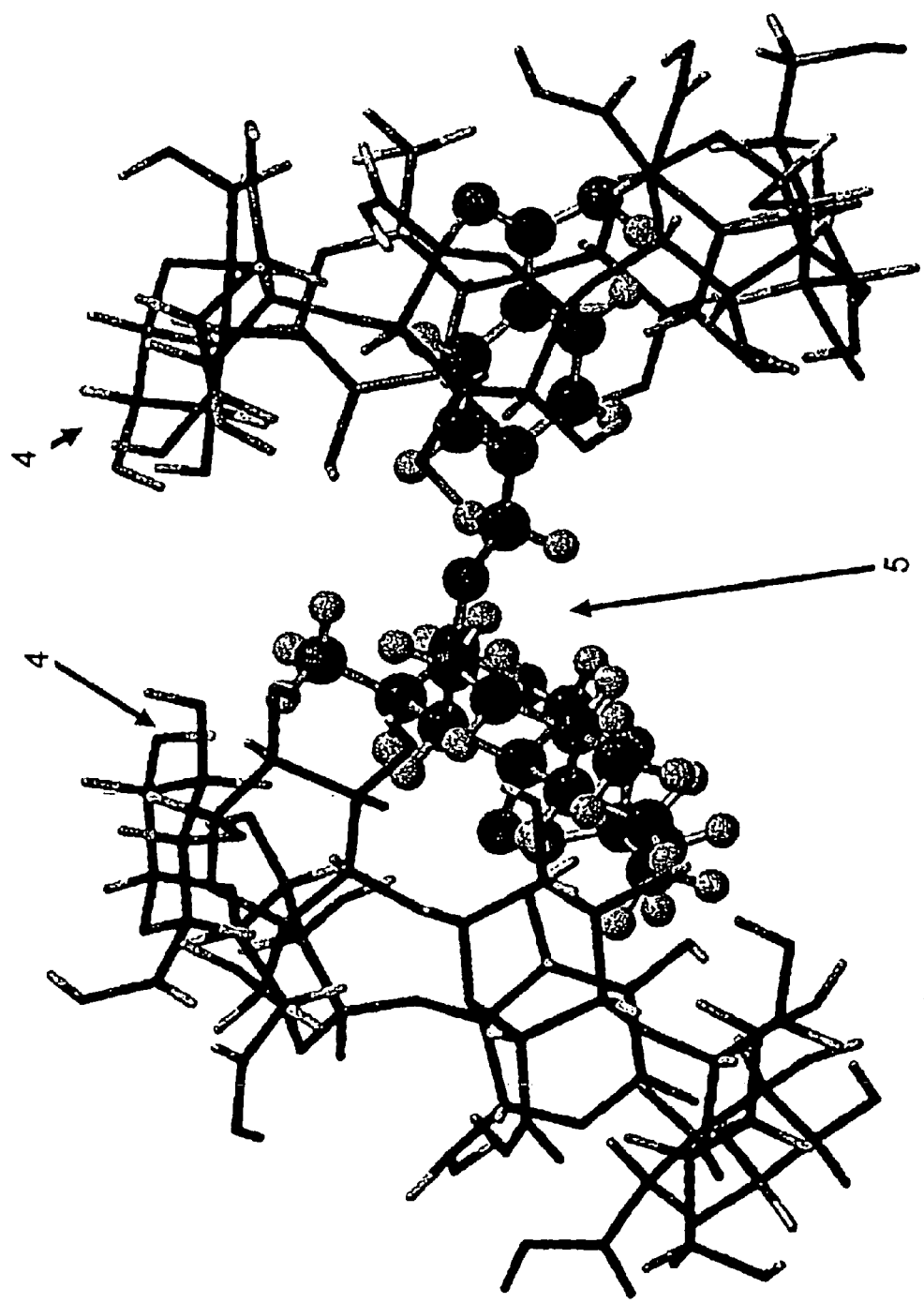
FIG. 21 is a molecular model of β-cyclodextrin complexed with artelinic acid in a 2:1 molecular ratio showing degrees of insertion and interaction between each molecule.

FIG. 20 clearly demonstrates the 2:1 complexation of β-cyclodextrin with artelinic acid. Two β-cyclodextrin molecules are shown at 4 and one artelinic acid molecule is shown at 5. The depth of insertion of the carboxylic acid tail compared to the peroxide bridge portion of the molecule is more clearly illustrated in the corresponding ball-and-stick model of the complex in FIG. 21 wherein two β-cyclodextrin molecules are shown at 4 and one artelinic acid molecule is shown at 5.

Figure 22:
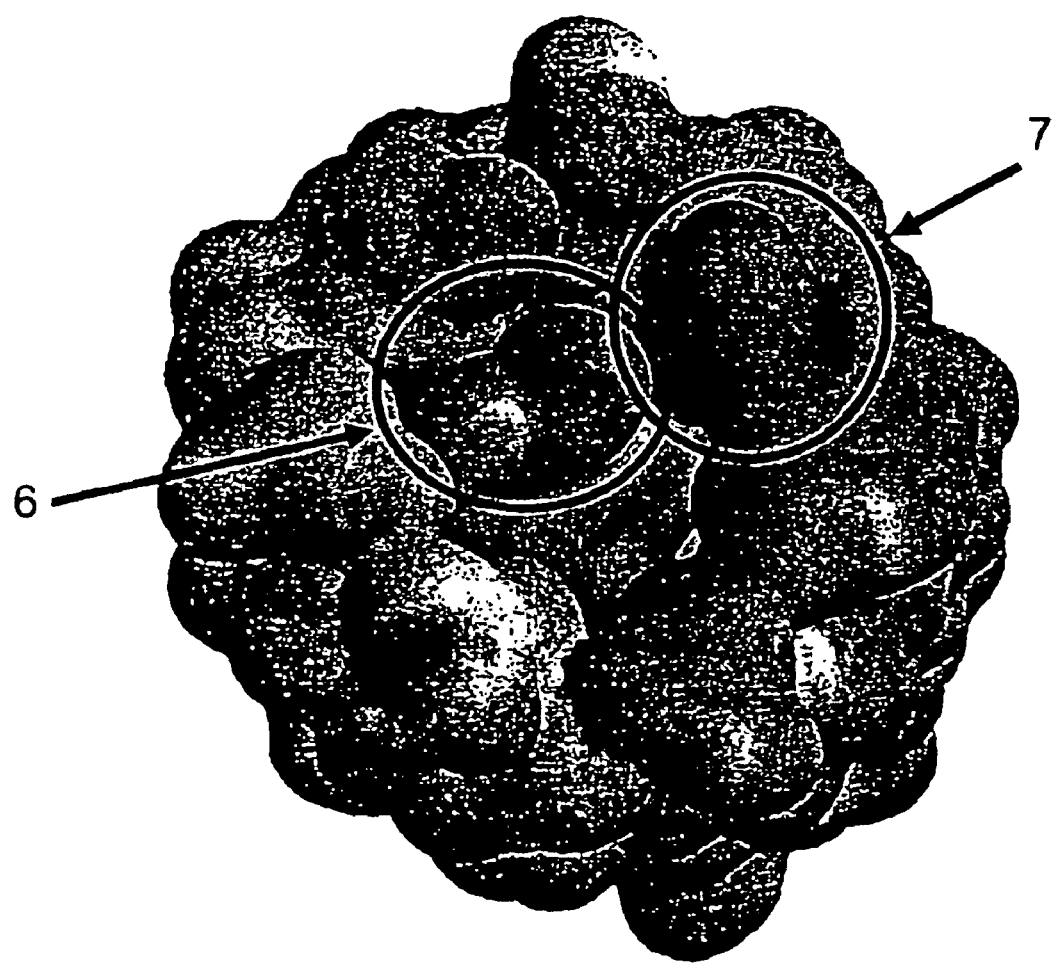
FIG. 22 is an axial view from the primary face of the electrostatic potential map of β-cyclodextrin complexed with artelinic acid in a 2:1 molecular ratio indicating the electrostatic interaction between the benzoic acid moiety and one of the cyclodextrins.

Lastly, FIG. 22 directly illustrates the unique physicochemical interaction of the electrostatc potential map of cyclodextrin with that of the artelinic acid tail. This axial view into the primary face of the second cyclodextrin molecule clearly illustrates this unique and selective electrostatic interaction. The negative region of the electrostatic potential map is shown at 6 and the positive region of electrostatic potential map is shown at 7.

Simple docking calculations do not yield these results as they assume an in vacuo environment. Inclusion complexes with cyclodextrins are mediated by the release of high-energy water molecules from the inner core of the cyclodextrin molecule. Therefore, direct structural measurements of the complex by techniques such as high resolution multi-dimensional NMR rationalized by physicochemical property determinations such as but not limited to molecular electrostatic potential mapping is specifically required to accurately characterize these complexes.

Osmometry Determinations.

Solutions of hydroxypropyl-β-cyclodextrin and artelinic acid of varied compositions as indicated were measured at room temperature using a Fiske ONE-TEN Osmometer (Fiske Associates, Norwood Mass., USA). The solvent for all experiments was ultra-pure distilled deionized water (18 MΩ) filtered through a 0.45 μm filter. Small sample volumes (15 μL) were measured in units of mOsmol/kg water with an instrument repeatability of ±2 mOsmol/kg water in the data range studied (0 to 400 mOsmol/kg water). The instrument was calibrated routinely with NIST standards of NaCl and a daily NIST reference of NaCl was verified at the start of each set of experiments.

Figure 23:
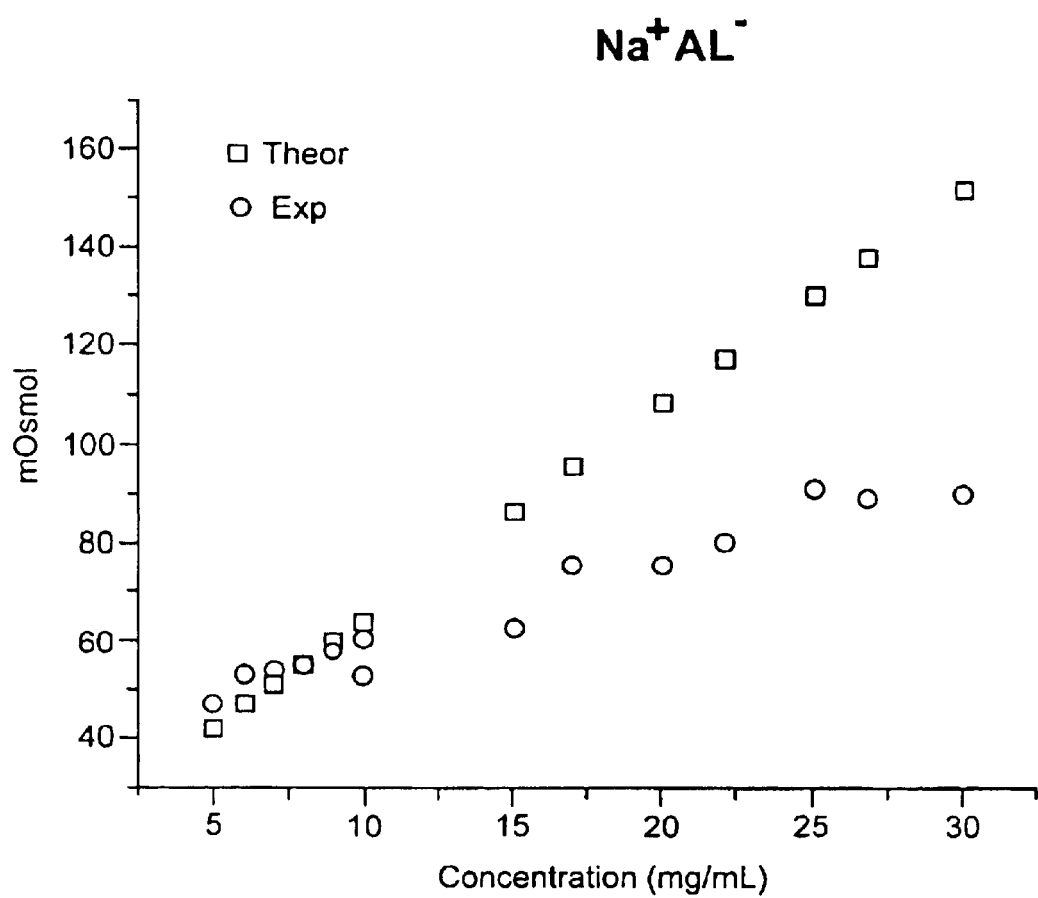
FIG. 23 is a plot of osmolality versus concentration of artelinate in aqueous solution compared to theoretical determinations based on the complete disassociation of the salt.

Osmolality is a direct measure of the degree of molecular dissociation of a species in water. FIG. 23 illustrates the deviation of measured osmolality in aqueous artelinate solutions versus theoretical calculations which assume complete dissociation. This deviation from ideality also appears to have a significant margin of error as observed by the marked degree of data scatter in the measurements.

Figure 24:
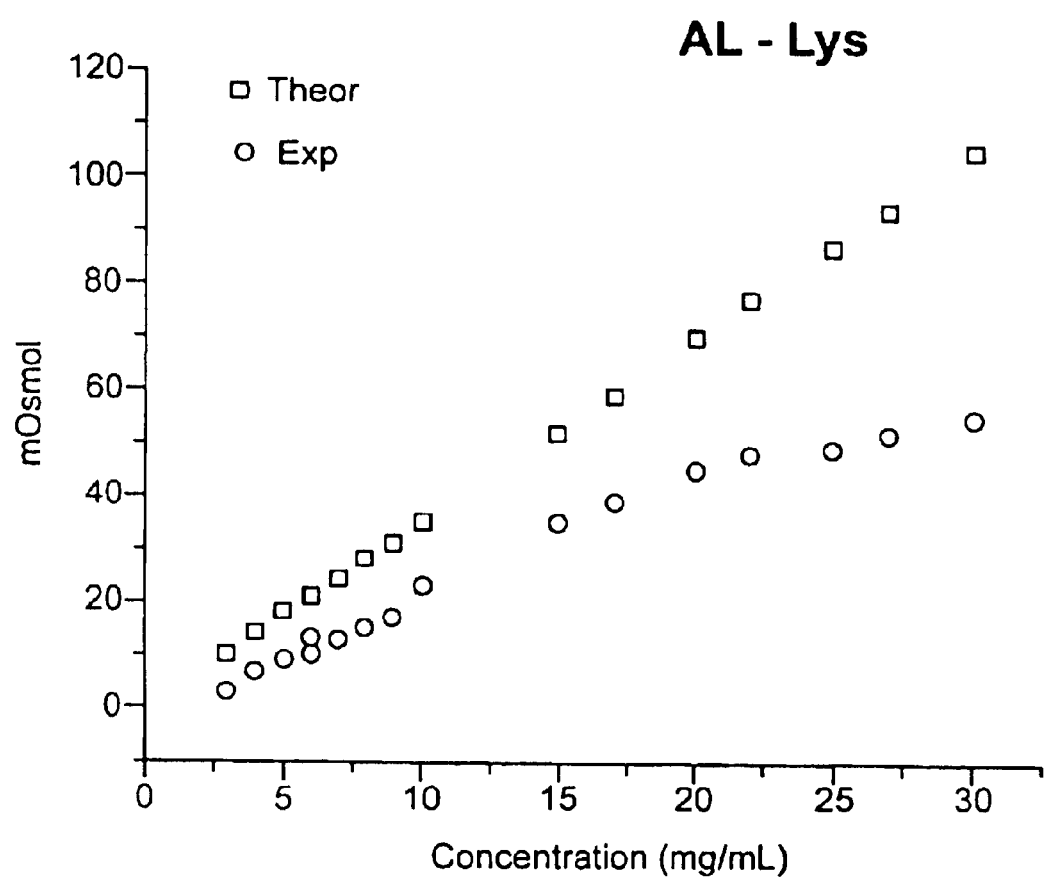
FIG. 24 is a plot of osmolality versus concentration of a lysine-artelinate salt preparation in aqueous solution compared to theoretical determinations based on the complete disassociation of the salt.
Figure 25:
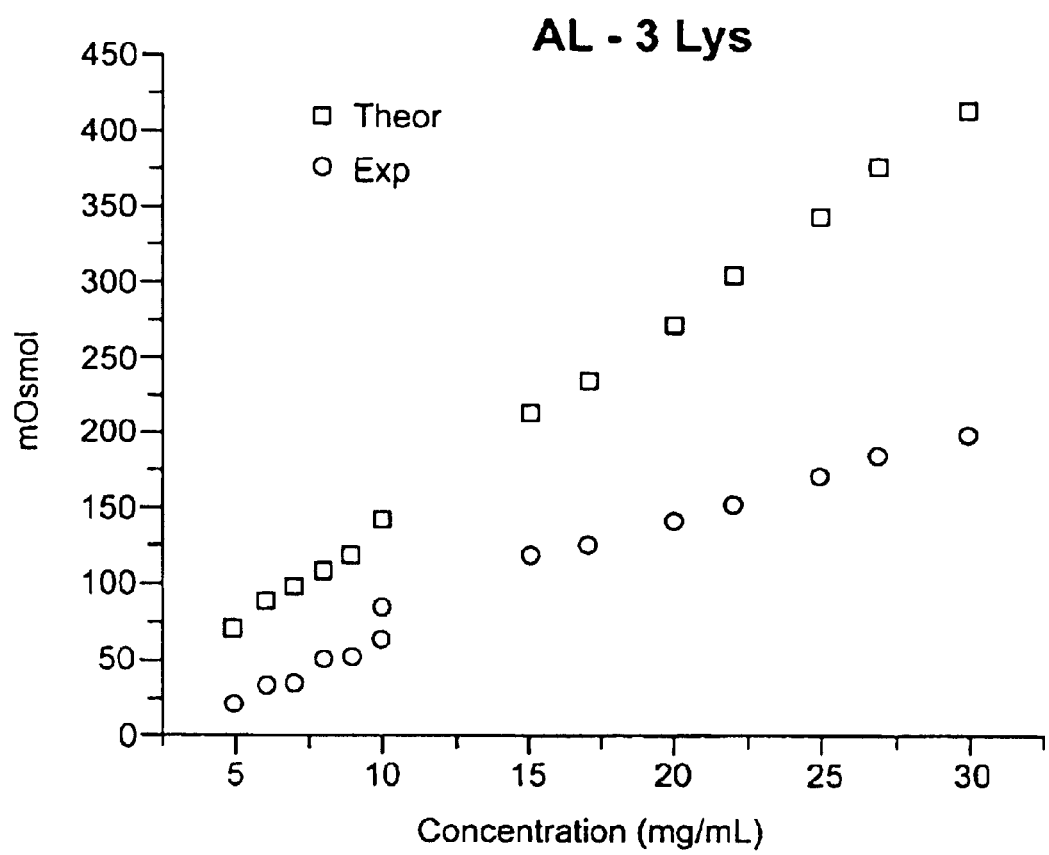
FIG. 25 is a plot of osmolality versus concentration of a lysine-artelinate salt preparation with 3 molar equivalents of lysine in aqueous solution compared to theoretical determinations based on complete disassociation of the salt.

FIGS. 24 and 25 illustrate a similar relationship between measured osmolality and ideal dissociation with a lysine salt formulation and a lysine salt formulation with 3 molar equivalents excess lysine. All three artelinate formulations appear to deviate strongly from ideality. Secondly, the measure of osmolality versus concentration of artelinate appears to be biphasic as demonstrated most clearly in FIG. 25, but also observed in FIGS. 23 and 24.

Figure 26:
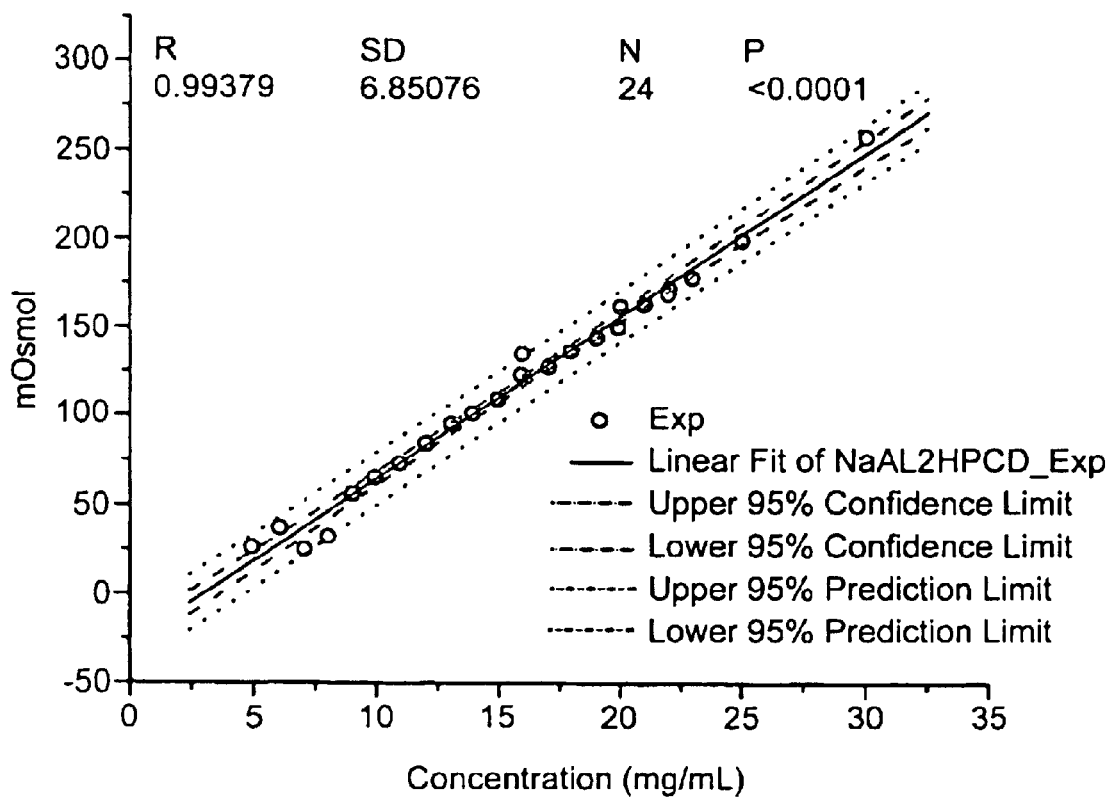
FIG. 26 is the linear regression (R=0.994, p<0.0001) of experimentally measured osmolality of artelinate complexed with hydroxypropyl-β-cyclodextrin (1:2 mole ratio) in aqueous solution. Upper and lower 95% confidence intervals and 95% prediction limits are also indicated.

FIG. 26 illustrates the strong linear correlation of the experimentally measured osmolality of artesunate complexed with hydroxypropyl-β-cyclodextrin in aqueous solutions. Hydroxypropyl-β-cyclodextrin was chosen for all osmolality determinations, as its aqueous solubility is greater than β-cyclodextrin and its well-established pharmacological compatibility for future i.v. drug formulations.

Measured deviation in osmolality of the artelinic acid-cyclodextrin (1:2) formulation after 28 days at room temperature was <7% in the concentration range of 15–25 mg/mL artelinate. This 7% deviation was consistently observed as an increase in osmolality due to an enhancement of solvation over time, rather than a decrease in solubility. The more concentrated solutions of cyclodextrin complexes would need to incubate for longer periods of time to ensure maximum complexation.

Figure 27A:
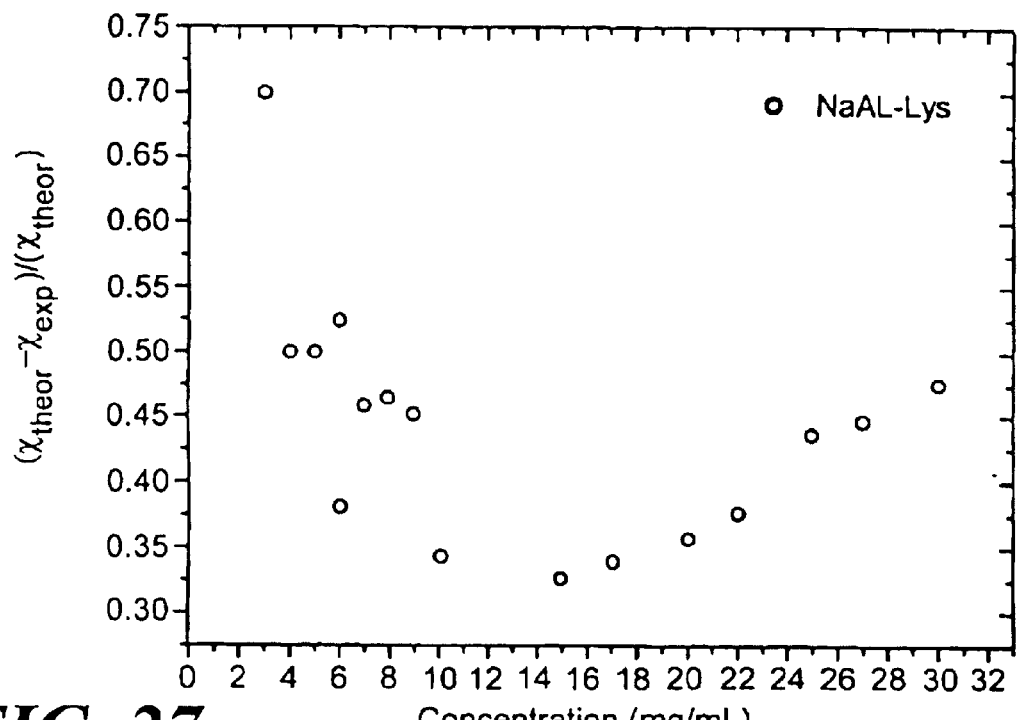
FIG. 27a–c are plots of relative deviation between experimentally measured osmolality and theoretical determinations based on complete disassociation for 3 aqueous artelinate formulations: lysine-artelinate prepared with 1 molar equivalent of lysine, lysine-artelinate prepared with 3 molar equivalents of lysine, and hydroxypropyl-β-cyclodextrin-artelinate (2:1) complex.
Figure 27B:
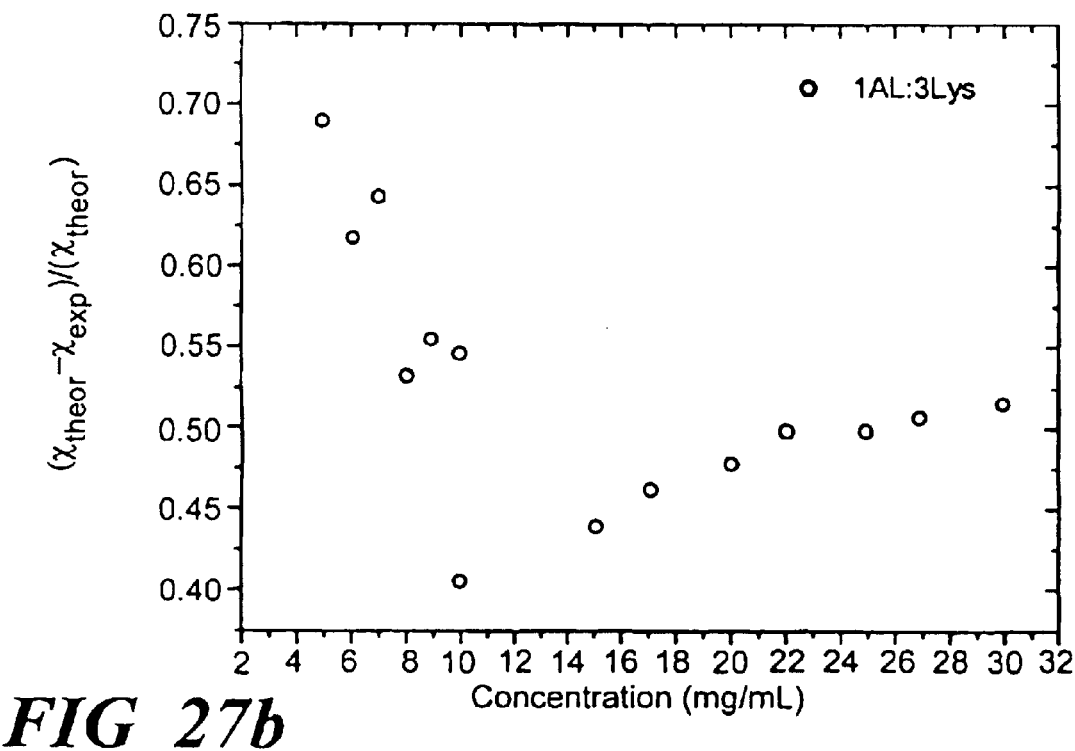
Figure 27C:
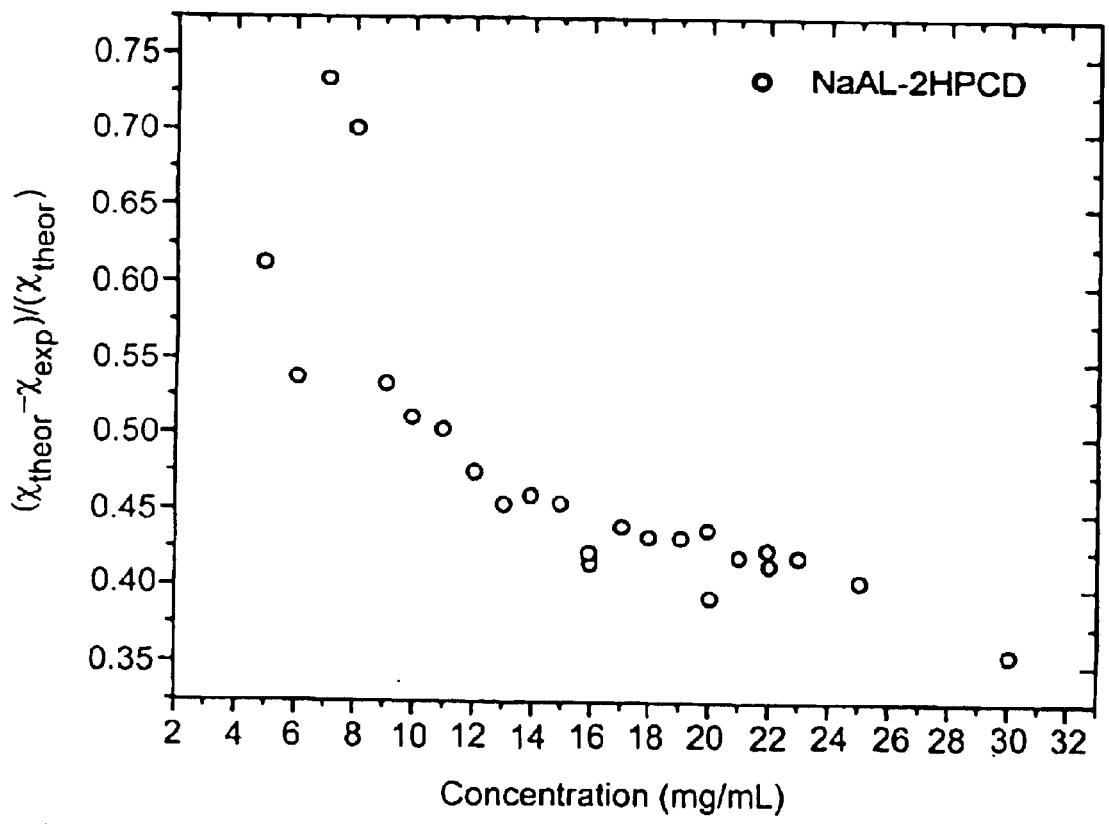

FIGS. 27a–c illustrate the deviations from ideality of three artelinate formulations, 1 molar equivalent of lysine shown at FIG. 27a, lysine-artelinate prepared with 3 molar equivalens of lysine shown at FIG. 27b and cyclodextrin-artelinate (2:1) complex shown at FIG. 27c. The artelinate-cyclodextrin formulation clearly deviates from ideality in a more predictable manner. The decrease in relative deviation with increasing concentration is mostly likely due to enhanced complexation due to a Le Chatelier's shift in solution equilibrium. This is notably contrasted with the other two formulations which yield solutions that deviate in an increasing manner (10–15%) from 12 to 30 mg/mL.

Injectable Formulation:

The stable form of artemisinin, the cyclodextrin complexed with artenilate in a 2:1 ratio, may be dissolved in saline, phosphate buffered saline (PBS), deionized water or any other suitable aqueous carrier for injection. The pH is preferably about 7.4. Generally, 40 milligrams of artelinate complexed with cyclodextrin per milliliter of solution is suitable. A dose of about 4–6 mg of artelinic acid (in complex) per kilogram of weight for a human is an appropriate dose. An injection of 10 ml of complex in solution or less is appropriate for treatment.

The formulation of the cyclodextrin complexed with artelinate in solution can be prepared and pumped through a filter into an injection vile, freeze dried for storage and later rehydrated with sterile water or saline or PBS for injection. The cyclodextrin complexed with artelinate in solution can also be administered orally, sublingually, or in the form of a suppository.

Toxicity:

Cyclodextrins and artemisinins are both non-toxic to humans. However, large doses of cyclodextrins are not implicated in cases where kidneys are not fully functional.

In Vitro Data

In Vitro Inhibition of *Plasmodium falciparum*.

See U.S. Pat. No. 6,284,772, which is herein incorporated by reference. The in vitro assays were conducted by using a modification of the semiautomated microdilution technique of Desjardins, et al. (1979) *Antimicrob. Agents Chemther.* 16:710–718 and Chulay et al. (1983) *Exp. Parasitol.* 55:138–146. Two strains of *Plasmodium falciparum* clones, from CDC Indochina III (W-2), CDC Sierra Leone I (D-6).

The W-2 clone is susceptible to mefloquine but resistant to chloroquine, sulfadoxine, pyrimethamine, and quinine. The D-6 clone is resistant to mefloquine but susceptible to chloroquine, sulfadoxine, pyrimethamine, and quinine. These clones were derived by direct visualization and micro-manipulation from patient isolates. Test compounds were initially dissolved in DMSO and diluted 400-fold in RPMI 1640 culture medium supplemented with 25 mM HEPES, 32 mM HaHCO$_3$, and 10% Albumax I (GIBCO BRL, Grand Island, N.Y.). These solutions were subsequently serially diluted 2-fold with a Biomek 1000 (Beckman, Fullerton, Calif.) over 11 different concentrations. The parasites were exposed to serial dilutions of each compound for 48 h and incubated at 37° C. with 5% O$_2$, 5% CO$_2$, and 90% N$_2$ prior to the addition of [$^3$H]hypoxanthine. After a further incubation of 18 h, parasite DNA was harvested from each microtiter well using Packard Filtermate 196 Harvester (Meriden, Conn.) onto glass filters. Uptake of [$^3$H]hypoxanthine was measured with a Packard Topcount scintillation counter. Concentration-response data were analyzed by a nonlinear regression logistic dose-response model, and the IC$_{50}$ values (50% inhibitory concentrations) for each compound were determined.

Figure 28:
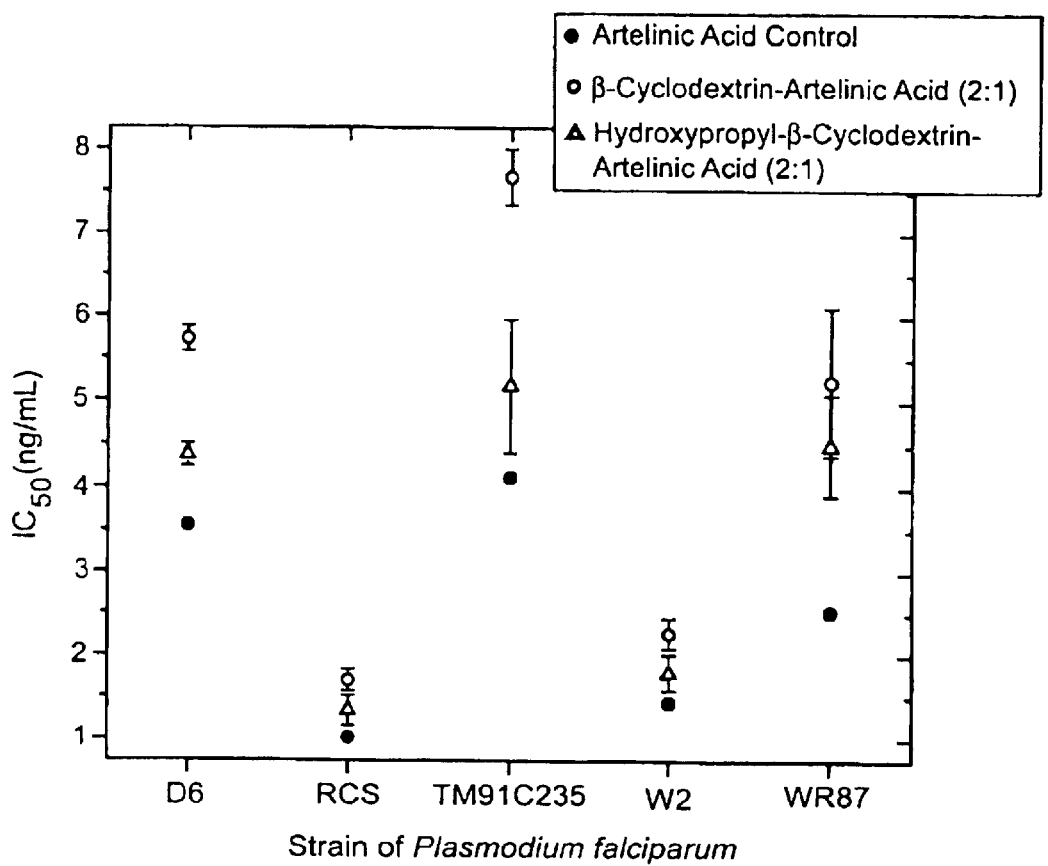
FIG. 28 is a graph showing $IC_{50}$ values of E-Cyclodextrin-Artelinic Acid (2:1) and Hydrowypropyl-E-Cyclodextrin-artelinic Acid (2:1) against *Plasmodium falciparum*.

FIG. 28 indicates that both cyclodextrin formulations of artelinic acid (β-cyclodextrin and hydroxypropyl-β-cyclodextrin) yielded very similar in vitro activity against multi-drug resistant strains of malaria as indicated. All data indicated IC$_{50}$ concentrations within 4 ng/mL of the uncomplexed artelinate salt (artelinic acid control). Therefore, complexation of the artemisinin molecule was not found to inhibit antimalarial efficacy.

Advantages

The complexed cyclodextrin-artemisinins formulation does not precipitate or degrade over time. Formulations of artemisinins and cyclodextrin have been observed to remain completely soluble for up to seven weeks at elevated physiological temperatures (40 degrees C.) without any degradation and up to 6 months at room temperature. The complexed cyclodextrin formulation of the artemisinins does not change color over time. Formulations of artemisinins and cyclodextrin have been observed to remain colorless for several weeks at elevated physiological temperatures of 40 degrees C.

EXAMPLES

Example 1

Formation of Artelinic Acid/Cyclodextrin Complex

Measure 2 moles of cyclodextrin and pre-dissolve in buffer, deionized water, or saline. Sonicate the mixture to completely dissolve the cyclodextrin. Add 1 mole equivalent of artelinic acid and sonicate. Incubate at 40° C. for 2–3 hours. Higher concentrations of artelinic acid require longer incubation times, such as overnight, to promote complexation.

Example 2

Formation of Artesunic Acid/Cyclodextrin Complex

Measure 1 mole of cyclodextrin and pre-dissolve in buffer, deionized water, or saline. Sonicate the mixture to completely dissolve the cyclodextrin. Add 1 mole equivalent of artesunic acid and sonicate. Incubate at 40° C. for 2–3 hours. Higher concentrations of artesunic acid require longer incubation times to promote complexation.

The use of the complexed cyclodextrin formulation of the artemisinins described provides a shielding effect to protect the body from local toxic effects from the antimalarial agent until the drug is diluted sufficiently into the system.

The process of making the complexed artemisinins of the invention can be performed on a large scale using similar conditions.

Having now fully described the invention, it will be apparent to one of ordinary skill in the art that many changes and modifications can be made thereto without departing from the spirit or scope of the invention as set for the herein.

What is claimed is:

1. A composition comprising: cyclodextrin complexed with artelinic acid in a 2:1 molar ratio.

2. A composition comprising cyclodextrin complexed with artelinic acid in a 2:1 molar ratio wherein said artelinic acid of said composition has a peroxide bridge and said cyclodextrin is coordinated to shield said peroxide bridge from hydrolytic decomposition.

3. The composition of claim 1, wherein said cyclodextrin is selected from the group consisting of alpha-cyclodextrin, beta-cyclodextrin and gama-cyclodextrin.

4. The composition of claim 1, wherein said cyclodextrin is beta-cyclodextrin selected from a group of beta-cyclodextrin analogs with similar complexing capabilities consisting of hydroxypropyl-beta-cyclodextrin, sulfobutyl ether-beta-cyclodextrin, and heptakis(2,6-di-O-methyl)-beta-cyclodextrin.

5. The composition of claim 1, further comprising an aqueous solution wherein said composition is dissolved in said aqueous solution.

6. The composition of claim 5, having a pH of 7.4.

7. The composition of claim 5, wherein said aqueous solution is selected from the group consisting of deionized water, saline solution, or phosphate buffered saline.

8. A stable artemisinin formulation comprising: beta-cyclodextrin complexed with artelinic acid in a 2:1 molar ratio, wherein said one of said beta-cyclodextrin shields a peroxide portion of the artemisinin and a second of said beta-cyclodextrin is complexed with an aromatic benzoic acid portion of the artemisinin.

9. The stable artemisinin formulation of claim 8, further comprising an aqueous solution wherein said formulation is dissolved in said aqueous solution.

10. The stable artemisinin formulation of claim 9, having a pH of 7.4.

11. The stable artemisinin formulation of claim 9, wherein said aqueous solution is selected from the group consisting of deionized water, saline solution, or phosphate buffered saline.

12. An antimalaria composition comprising: an antimalaria effective amount of a complexed cyclodextrin formulation of artemisinin, wherein said cyclodextrin is complexed with artelinic acid in a 2:1 molar ratio in aqueous solution.

13. The antimalaria composition of claim 12, wherein said composition is stable in solution for up to 7 weeks at 40° C.

14. The antimalaria composition of claim 12, wherein said composition has a pH of about 7.4.

15. The antimalaria composition of claim 12, wherein said composition is in a form of an intravenous dose, oral dose, sublingual dose, or suppository.

16. An antimalarial composition comprising:

an antimalaria amount of a complexed cyclodextrin formulation of artemisinin, wherein said cyclodextrin is complexed with artesunic acid in a 1:1 molar ratio in an aqueous solution.

17. The antimalarial composition of claim 16, wherein said composition is stable in solution for up to 7 weeks at 40° C.

18. The antimalarial composition of claim 16, wherein said composition has a pH of about 7.4.

19. The antimalarial composition of claim 16, wherein said composition is in a form of an intravenous dose, oral dose, sublingual dose, or suppository.

20. A composition comprising: cyclodextrin complexed with artesunic acid in a 1:1 molar ratio.

21. The antimalaria composition of claim 20, wherein said cyclodextrin is selected from the group consisting of alpha-cyclodextrin, beta-cyclodextrin and gama-cyclodextrin.

22. The composition of claim 20, wherein said cyclodextrin is beta-cyclodextrin selected from a group of beta-cyclodextrin analogs with similar complexing capabilities consisting of hydroxypropyl-beta-cyclodextrin, sulfobutyl ether-beta-cyclodextrin, heptakis(2,6-di-O-methyl)-beta-cyclodextrin.

23. The composition of claim 20, further comprising an aqueous solution wherein said composition is dissolved in said aqueous solution and is stable in said aqueous solution.

24. The composition of claim 23, having a pH of 7.4.

25. The composition of claim 23, wherein said aqueous solution is selected from the group consisting of deionized water, saline solution, or phosphate buffered saline.

26. A stable artemisinin formulation comprising: beta-cyclodextrin complexed with artesunic acid in a 1:1 ratio, wherein said beta-cyclodextrin shields a peroxide portion of the artemisinin.

27. A composition comprising cyclodextrin complexed with artesunic acid in a 1:1 molar ratio, wherein said artesunic acid of said composition has a peroxide bridge and said cyclodextrin is coordinated to shield said peroxide bridge.

* * * * *